US006146628A

United States Patent [19]

Uckun et al.

[11] Patent Number: 6,146,628

[45] Date of Patent: Nov. 14, 2000

[54] BIOTHERAPEUTIC AGENTS COMPRISING RECOMBINANT PAP AND PAP MUTANTS

[75] Inventors: Fatih M. Uckun, White Bear Lake, Minn.; Nilgun E. Tumer, Belle Mead, N.J.

[73] Assignees: Regents of the University of Minnesota and Rutgers, Minneapolis, Minn.; The State University of New Jersey, Piscataway, N.J.

[21] Appl. No.: 08/501,253

[22] Filed: Jul. 11, 1995

[51] Int. Cl.[7] ........................ A61K 39/395; A61K 39/40; A61K 39/42; A61K 39/44

[52] U.S. Cl. .................................... 424/134.1; 424/142.1; 424/143.1; 424/147.1; 424/148.1; 424/183.1; 424/184.1; 424/187.1

[58] Field of Search ............................. 424/134.1, 183.1, 424/142.1, 143.1, 147.1, 148.1, 184.1, 187.1

[56] References Cited

U.S. PATENT DOCUMENTS

| | | | |
|---|---|---|---|
| 4,340,535 | 7/1982 | Voisin et al. . | |
| 4,363,758 | 12/1982 | Masuho et al. . | |
| 4,671,958 | 6/1987 | Rodwell . | |
| 4,831,117 | 5/1989 | Uckun . | |
| 5,167,956 | 12/1992 | Neville, Jr. et al. . | |
| 5,304,730 | 4/1994 | Lawson et al. . | |
| 5,690,935 | 11/1997 | Uckun et al. ........................ | 424/183.1 |

FOREIGN PATENT DOCUMENTS

| | | |
|---|---|---|
| 2699553 A1 | 6/1994 | France . |

OTHER PUBLICATIONS

Abel et al., Science 232: 738–43 (1986).
Aron et al., *Antimicrob. Agents Chemotherapy*, 17, 1032 (1980).
Bolognesi, et al., *Clin. Exp. Immunol.* 89:341 (1992).
Bruland, et al., *Int. J. Cancer* 38:27 (1986).
Bruland, *Cancer Res* 48:5302 (1988).
Bruland and Pihl, In: *Frontiers of Osteosarcoma Research* (1993).
Byers, et al., *AIDS*, 4, 1189 (1990).
Cannistern, et al., *J.B. Chem.* 265:12656(1990).
Chelstrom et al., *Blood*, 84, 20 (1994).
Endo et al., Biophys. Res. Comm., 150:1032–36 (1988).
Erice et al., *Antimicrob. Ag. Chemother.*, 37, 835 (1993).
Erice et al., *J. Clin. Microbiol.*, 30, 444 (1992).
Golemboski et al., Proc. Natl. Acad. Sci. USA 87:6311–15 (1990).
Gould et al., *J. Natl. Cancer Inst.*, 81, 775 (1989).
Gunther, et al., *Blood* 85:2537–2545 (May 1995).
Hartley et al., FEBS Lett. 290:65–68 (1991).
Hayashi et al., J. Bioenerg. Biomem. 22:451–71 (1990).
Hemenway et al., EMBO J. 7:1273–80 (1988).
Higashigawa, et al., *Leukemia Research* 16:1049(1992).
Houston, et al., In: *Immunological Antibody Conjugates in Radioimaging and Therapy of Cancer*, Vogel ed. NY, Oxford Univ. Press, p. 71 (1987).
Hoxie et al., *Science*, 234, 1123 (1986).
Irvin, et al., *Pharmacol. and Therapeutics* 55:279(1992).
Ito et al., *J. Bacteriol.*, 153, 163 (1983).
Jackson et al., *J. Clin. Microbiol.*, 28, 16 (1990).
Lee, et al., *Nature* 289:407(1981).
Lee–Huang et al., *FEBS Lett.*, 272, 12 (1990).
Linsley et al., *J. Virol.*, 62, 3695 (1988).
Lodge et al., Proc. Natl. Acad. Sci. USA 90:7089–93 (1993).
Meyers et al., *Journal of Immunological Methods*, 136, 221 (1991).
Monzingo et al., *J. Molecular Biol.*, 233, 705 (1993).
Mosier et al., *Science*, 251, 791 (1991).
Myers, et al., *J. Immunol. Methods* 136:221–238(1991).
Olson et al., *AIDS Res. Human Retroviruses*, 7, 1025 (1991).
Pastan, et al., *Science*, 254:1173(1991).
Saksela et al., *Proc. Natl. Acad. Sci. U.S.A.*, 91, 1104 (1994).
Schnittman et al., *Science*, 245, 305 (1989).
Soler–Rodriguez et al., *Experimental Cell Research*, 206, 227 (1993).
Stevens et al., *Experientia*, 37, 257 (1981).
Teltow et al., *Antimicrob. Ag. Chemother.*, 23, 390 (1983).
Thorpe, *Cancer Res.* 47:5924(1987).
Uckun, et al., In: *Human Tumor Antigens and Specific Tumor Therapy*, UCLA Symposium Molecular Cellular Biology, New Ser (1989) pp. 231–241.
Uckun, et al., *J. Exp. Med.* 163:347(1986).
Uckun, et al., *Proc. Natl. Acad. Sci. U.S.A.*, 85, 8603 (1988).
Uckun, et al., *Blood* 71:13 (1988).
Uckun, et al., *Blood*, 76, 1723 (1990).
Uckun, et al., *Blood*, 76, 1908 (1990).
Uckun, et al., Third Int'l. Symposium on Immunotoxins, p. 131(1992).
Uckun, et al., *Blood* 79:2201(May 1992).
Uckun, et al., *Blood* 79:3116 (Jun. 1992).
Uckun, et al., *Blood* 79:3369 (Jun. 1992).
Uckun, et al., *Br. J. Haemotol* 85:435(1993).
Uckun, et al., *Leukemia* 7:341 (1993).
Uckun, et al., *Leukemia and Lymphoma* 9:459–476 (Apr. 1993).
Ussery et al., *Ann, N. Y. Acad. Sci*, 284, 431 (1977).
Van Leeuwen, et al., *Blood* 73:1142(1989).
Yang, et al., *Cell* 47:3(1986).
Zarling et al. *Nature*, 347, 92 (1990).
Uckun, et al.: A clinical phase I dose escalation . . .: Program and Abstracts Third Intern. Symp. on Immuno.: p. 131, Jun. 1992.
Jain, et al. : Barriers to drug delivery in solid tumors: Sci. Am. : 271(1): pp. 58–65, Jul. 1994.

(List continued on next page.)

*Primary Examiner*—Jeffrey Stucker
*Assistant Examiner*—Brett Nelson
*Attorney, Agent, or Firm*—Merchant & Gould P.C.

[57] ABSTRACT

Biotherapeutic agents are provided which comprise recombinant PAP or a biologically equivalent variant or mutant thereof, linked to a targeting moiety which are effective for the treatment of certain human diseases. The invention further provides a process for producing the biotherapeutic agents as well as a method which utilizes the disclosed biotherapeutic agents to systemically treat cancer patients.

12 Claims, No Drawings

OTHER PUBLICATIONS

Osband et al. : Problems in the investigational study and . . .: Immunol. Tod. : 11(6): pp. 193–195, 1990.

Myers, et al. : Production of a pokeweed antiviral protein . . .: J. Immun. Meth.: 136: pp. 221–238, 1991.

Zarling, et al. : Inhibition of HIV replication by pokeweed . . .: Nature: v. 347: pp. 92–95, Sep. 1990.

Burgess, et al. : Possible dissociation of the heparin–binding . . .: J. Cell Bio.: vol. 111: pp. 2129–2138, 1990.

Lazar, et al. : Transforming growth factor . . .: Mol. Cell. Bio. : vol. 8, No. 3: pp. 1247–1252, Mar. 1988.

Tao, et al. : Studies of aglycosylated chimeric . . .: J. Immun. : vol. 143, No. 8: pp. 2595–2601, Oct. 1989.

```
                              SEQUENCE LISTING

(1) GENERAL INFORMATION:

   (iii) NUMBER OF SEQUENCES: 21


(2) INFORMATION FOR SEQ ID NO:1:

     (i) SEQUENCE CHARACTERISTICS:
          (A) LENGTH: 1379 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 225..1163

    (xi) SEQUENCE DESCRIPTION: SEQ ID NO:1:

CTATGAAGTC GGGTCAAAGC ATATACAGGC TATGCATTGT TAGAAACATT GATGCCTCTG      60

ATCCCGATAA ACAATACAAA TTAGACAATA AGATGACATA CAAGTACCTA AACTGTGTAT     120

GGGGGAGTGA AACCTCAGCT GCTAAAAAAA CGTTGTAAGA AAAAAAAGAA GTTGTGAGTT     180

AACTACAGGG CGAAAGTATT GGAACTAGCT AGTAGGAAGG GAAG ATG AAG TCG ATG      236
                                                 Met Lys Ser Met
                                                   1

CTT GTG GTG ACA ATA TCA ATA TGG CTC ATT CTT GCA CCA ACT TCA ACT       284
Leu Val Val Thr Ile Ser Ile Trp Leu Ile Leu Ala Pro Thr Ser Thr
  5                  10                  15                  20

TGG GCT GTG AAT ACA ATC ATC TAC AAT GTT GGA AGT ACC ACC ATT AGC       332
Trp Ala Val Asn Thr Ile Ile Tyr Asn Val Gly Ser Thr Thr Ile Ser
                 25                  30                  35

AAA TAC GCC ACT TTT CTG AAT GAT CTT CGT AAT GAA GCG AAA GAT CCA       380
Lys Tyr Ala Thr Phe Leu Asn Asp Leu Arg Asn Glu Ala Lys Asp Pro
             40                  45                  50

AGT TTA AAA TGC TAT GGA ATA CCA ATG CTG CCC AAT ACA AAT ACA AAT       428
Ser Leu Lys Cys Tyr Gly Ile Pro Met Leu Pro Asn Thr Asn Thr Asn
         55                  60                  65

CCA AAG TAC GTG TTG GTT GAG CTC CAA GGT TCA AAT AAA AAA ACC ATC       476
Pro Lys Tyr Val Leu Val Glu Leu Gln Gly Ser Asn Lys Lys Thr Ile
     70                  75                  80

ACA CTA ATG CTG AGA CGA AAC AAT TTG TAT GTG ATG GGT TAT TCT GAT       524
Thr Leu Met Leu Arg Arg Asn Asn Leu Tyr Val Met Gly Tyr Ser Asp
 85                  90                  95                 100

CCC TTT GAA ACC AAT AAA TGT CGT TAC CAT ATC TTT AAT GAT ATC TCA       572
Pro Phe Glu Thr Asn Lys Cys Arg Tyr His Ile Phe Asn Asp Ile Ser
                105                 110                 115

GGT ACT GAA CGC CAA GAT GTA GAG ACT ACT CTT TGC CCA AAT GCC AAT       620
Gly Thr Glu Arg Gln Asp Val Glu Thr Thr Leu Cys Pro Asn Ala Asn
            120                 125                 130

TCT CGT GTT AGT AAA AAC ATA AAC TTT GAT AGT CGA TAT CCA ACA TTG       668
Ser Arg Val Ser Lys Asn Ile Asn Phe Asp Ser Arg Tyr Pro Thr Leu
        135                 140                 145

GAA TCA AAA GCG GGA GTA AAA TCA AGA AGT CAG GTC CAA CTG GGA ATT       716
Glu Ser Lys Ala Gly Val Lys Ser Arg Ser Gln Val Gln Leu Gly Ile
```

-continued

```
    150                 155                 160

CAA ATA CTC GAC AGT AAT ATT GGA AAG ATT TCT GGA GTG ATG TCA TTC       764
Gln Ile Leu Asp Ser Asn Ile Gly Lys Ile Ser Gly Val Met Ser Phe
165                 170                 175                 180

ACT GAG AAA ACC CAA GCC GAA TTC CTA TTG GTA GCC ATA CAA ATG GTA       812
Thr Glu Lys Thr Gln Ala Glu Phe Leu Leu Val Ala Ile Gln Met Val
                185                 190                 195

TCA GAG GCA GCA AGA TTC AAG TAC ATA GAG AAT CAG GTG AAA ACT AAT       860
Ser Glu Ala Ala Arg Phe Lys Tyr Ile Glu Asn Gln Val Lys Thr Asn
            200                 205                 210

TTT AAC AGA GCA TTC AAC CCT AAT CCC AAA GTA CTT AAT TTG CAA GAG       908
Phe Asn Arg Ala Phe Asn Pro Asn Pro Lys Val Leu Asn Leu Gln Glu
        215                 220                 225

ACA TGG GGT AAG ATT TCA ACA GCA ATT CAT GAT GCC AAG AAT GGA GTT       956
Thr Trp Gly Lys Ile Ser Thr Ala Ile His Asp Ala Lys Asn Gly Val
    230                 235                 240

TTA CCC AAA CCT CTC GAG CTA GTG GAT GCC AGT GGT GCC AAG TGG ATA      1004
Leu Pro Lys Pro Leu Glu Leu Val Asp Ala Ser Gly Ala Lys Trp Ile
245                 250                 255                 260

GTG TTG AGA GTG GAT GAA ATC AAG CCT GAT GTA GCA CTC TTA AAC TAC      1052
Val Leu Arg Val Asp Glu Ile Lys Pro Asp Val Ala Leu Leu Asn Tyr
                265                 270                 275

GTT GGT GGG AGC TGT CAG ACA ACT TAT AAC CAA AAT GCC ATG TTT CCT      1100
Val Gly Gly Ser Cys Gln Thr Thr Tyr Asn Gln Asn Ala Met Phe Pro
            280                 285                 290

CAA CTT ATA ATG TCT ACT TAT TAT AAT TAC ATG GTT AAT CTT GGT GAT      1148
Gln Leu Ile Met Ser Thr Tyr Tyr Asn Tyr Met Val Asn Leu Gly Asp
        295                 300                 305

CTA TTT GAA GGA TTC TGATCATAAA CATAATAAGG AGTATATATA TATTACTCCA     1203
Leu Phe Glu Gly Phe
    310

ACTATATTAT AAAGCTTAAA TAAGAGGCCG TGTTAATTAG TACTTGTTGC CTTTTGCTTT   1263

ATGGTGTTGT TTATTATGCC TTGTATGCTT GTAATATTAT CTAGAGAACA AGATGTACTG   1323

TGTAATAGTC TTGTTTGAAA TAAAACTTCC AATTATGATG CAAAAAAAAA AAAAAA       1379
```

(2) INFORMATION FOR SEQ ID NO:2:

(i) SEQUENCE CHARACTERISTICS:
(A) LENGTH: 313 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Ser Met Leu Val Val Thr Ile Ser Ile Trp Leu Ile Leu Ala
  1               5                  10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
     50                  55                  60

Thr Asn Thr Asn Pro Lys Tyr Val Leu Val Glu Leu Gln Gly Ser Asn
 65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
```

-continued

```
            100                 105                 110

Asn Asp Ile Ser Gly Thr Glu Arg Gln Asp Val Glu Thr Thr Leu Cys
        115                 120                 125

Pro Asn Ala Asn Ser Arg Val Ser Lys Asn Ile Asn Phe Asp Ser Arg
    130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Gln Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Asn Tyr Val Gly Gly Ser Cys Gln Thr Thr Tyr Asn Gln Asn
        275                 280                 285

Ala Met Phe Pro Gln Leu Ile Met Ser Thr Tyr Tyr Asn Tyr Met Val
    290                 295                 300

Asn Leu Gly Asp Leu Phe Glu Gly Phe
305                 310
```

(2) INFORMATION FOR SEQ ID NO:3:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

GGCATGGGCG CTGATGATGT TGTTGATTC 29

(2) INFORMATION FOR SEQ ID NO:4:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

GCGTATTCTC CGGGGCATAA AATCGGGTGG AGGTGGCTCC ATGGC 45

(2) INFORMATION FOR SEQ ID NO:5:

(i) SEQUENCE CHARACTERISTICS:
(A) LENGTH: 33 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:5:

GCCATGGTTC AGCTGCAGCA GTCTGGGGCT GAG 33

(2) INFORMATION FOR SEQ ID NO:6:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

CCATGGCTAT GAGGAGACGG AGACTGAGGT TCCTTG 36

(2) INFORMATION FOR SEQ ID NO:7:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

GCCATGGACA TTGTGCTGAC CCAATCTCCA GCTTCC 36

(2) INFORMATION FOR SEQ ID NO:8:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

CCATGGCTAT TTGATTTCCA GCTTGGTGCC TCCACCGAAC G 41

(2) INFORMATION FOR SEQ ID NO:9:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO:9:

```
Gly Gly Gly Gly Ser Gly Gly Gly Gly Thr Gly Gly Gly Gly Ser
1               5                   10                  15
```

(2) INFORMATION FOR SEQ ID NO:10:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:10:

-continued

Gly Ser Thr Ser Gly Ser Gly Lys Ser Ser Glu Gly Lys Gly
1 5 10

(2) INFORMATION FOR SEQ ID NO:11:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

TCCGGAGGAG GCGGTACCGG TGGTGGCGGT AGCGACATTG TGCTGACCCA ATC 53

(2) INFORMATION FOR SEQ ID NO:12:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

CTGGTTCCGG AAAATCTTCT GAAGGTAAAG GTGACATTGT GCTGACCCAA TC 52

(2) INFORMATION FOR SEQ ID NO:13:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

ACCGGTACCG CCTCCTCCGG ATCCGCCTCC GCCTGAGGAG ACGGAGACTG 50

(2) INFORMATION FOR SEQ ID NO:14:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

GGCGGAGGCG GATCCGGAGG AGGCGGTACC GGTGGTGGCG GTAGC 45

(2) INFORMATION FOR SEQ ID NO:15:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

GGCGGAGGCG GATCCGGAGG AGGCGGTACC GGTGGTGGCG GTAGC 45

-continued (2) INFORMATION FOR SEQ ID NO:16:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

GGTTCTACCT CTGGTTCCGG AAAATCTTCT GAAGGTAAAG GT 42

(2) INFORMATION FOR SEQ ID NO:17:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

GGCATGGGCG CTGATGATGT TGTTGATTC 29

(2) INFORMATION FOR SEQ ID NO:18:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

GCGTATTCTC CGGGGCATAA AATCGGGTGG AGGTGGCTCC ATGGC 45

(2) INFORMATION FOR SEQ ID NO:19:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

ATAATCCACC TATCCCAGTA GGAGAAAT 28

(2) INFORMATION FOR SEQ ID NO:20:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

TTTGGTCCTT GTCTTATGTC CAGAATGC 28

(2) INFORMATION FOR SEQ ID NO:21:

(i) SEQUENCE CHARACTERISTICS:
(A) LENGTH: 41 base pairs

-continued

```
        (B) TYPE: nucleic acid
        (C) STRANDEDNESS: single
        (D) TOPOLOGY: linear

    (ii) MOLECULE TYPE: DNA (genomic)

    (xi) SEQUENCE DESCRIPTION: SEQ ID NO:21:

CCATGGCTAT TTGATTTCCA GCTTGGTGCC TCCACCGAAC G                              41
```

BIOTHERAPEUTIC AGENTS COMPRISING RECOMBINANT PAP AND PAP MUTANTS

GOVERNMENT SUPPORT

This development of this invention was supported in part by National Science Foundation Grant MCB-941919. The Government has certain rights in the invention.

BACKGROUND OF THE INVENTION

Drug targeting is a potentially attractive new approach to killing malignant cells, which can leave normal tissue unharmed. A decisive breakthrough in drug targeting was the advent of hybridoma technology, making many monoclonal antibodies (MoAb) available in essentially limitless supply. To construct therapeutic reagents with selectivity for certain populations of tumor cells, MoAbs or other cell targeting proteins are linked to cytotoxic agents to form agents referred to as immunoconjugates, immunotoxins or fusion proteins which can combine the selectivity of the targeting moiety with the potency of the bioactive moiety. The choice of monoclonal antibody (or other targeting moiety) is based on the surface antigen profile of a malignant cell.

For the past decade, these types of biotherapeutic agents have been under investigation for the treatment of various cancers, and more recently for the treatment of immunological disorders such as rheumatoid arthritis and AIDS. Although these biotherapeutic agents have shown some potential to provide safe and effective therapy for human disease, many difficulties remain. Ideally, consistently locatable and reliable markers on target cells would permit the binding portion of biotherapeutic agents to completely avoid non-target tissue. In reality, cross-reactivity with antigens expressed by vital life-maintaining organs often gives rise to unacceptable complications in in vivo applications. There is also the potential that patients will demonstrate immune responses to the separate components of the biotherapeutic agents even though they may already be immunosuppressed by the course of their disease. Moreover, the cytotoxicity obtained in in vitro studies may be limited in clinical application due to a lack of potency in doses that can be tolerated by the patient. Finally, solid tumors are difficult to penetrate thoroughly and in hematologic malignancies, residual disease can cause relapse despite easier access to target cells in leukemias and lymphomas.

Fusion proteins specifically are designed to solve problems incurred in the use of immunoconjugates or immunotoxins, while providing some additional benefits. For example, the native toxin may be in a limited supply and thus, increasingly expensive. Furthermore, the production of immunotoxins or immunoconjugates by chemical coupling methods can result in reduced activity of either or both of the toxin or the antibody portion. Additionally, biotherapeutic agents prepared by chemically linking a whole antibody to a toxin are large in size, typically having a molecular mass of 210,000 kDa. Because of the large size, these biotherapeutic agents have limited vascular and tissue penetration; particularly, they cannot pass the blood-brain barrier. Finally, because the chemical conjugation methods used produce heterogeneous products, these types of biotherapeutic agents can illicit significant non-specific systemic toxicity. Also contributing to this non-specific systemic toxicity is the large molecule size of biotherapeutic agents and their resulting long half-life.

Thus, there are serious and recurring problems with these types of biotherapeutic agents and their associated therapies. Therefore, there is continuing need for improved biotherapeutic agents and methods of their use to target and inhibit or eliminate cell populations associated with various pathologies.

SUMMARY OF THE INVENTION

The present invention provides a biotherapeutic agent, in one embodiment an immunotoxin, which comprises a targeting moiety, which binds to a receptor expressed on to the surface of a mammalian cell, linked to a cytotoxic agent. The targeting (or binding) moieties suitable for use in the present invention preferably do not bind to a receptor expressed on normal pluripotent bone marrow progenitor cells.

Preferably, the targeting moiety will be a monoclonal antibody, monoclonal antibody fragment, or an antibody-derived single chain variable region polypeptide, that binds to the surface of cancer cells or tumor blood vessels. Most preferably, the targeting moiety will be a monoclonal antibody, monoclonal antibody fragment, or single chain variable region polypeptide directed against the CD2, CD3, CD4, CD5, CD7, CD13, CD19, CD22, CD24, CD33, CD40, CD45, CD72, TXU.1, NXU.1, TP-1, or TP-3 antigen.

It is preferred that the cytotoxic agent of the present biotherapeutic agent is a bacterial or plant toxin. More preferably, the cytotoxic agent is recombinant pokeweed antiviral protein (PAP) or a functionally equivalent bioactive mutant or variant thereof. Most preferably, the cytotoxic agent is recombinant PAP comprising an amino acid sequence according to SEQ ID NO:2, SEQ ID NO:3, SEQ ID NO:4, SEQ ID NO:5, SEQ ID NO:6, SEQ ID NO:7, SEQ ID NO:8, or a biologically functional equivalent thereof.

The mammalian cell targeted by the PAP immunotoxin will preferably be a cancer cell or a cell on the surface of a tumor blood vessel. More preferably, if the cell will be one associated with leukemia, lymphoma, a brain tumor, neuroblastoma, osteosarcoma, soft tissue sarcoma, breast cancer, prostate cancer, ovarian cancer, testicular cancer, melanoma, lung cancer, or colon cancer.

In another embodiment, the present invention also provides a biotherapeutic agent, specifically a fusion polypeptide toxin, for the treatment of cancer comprising a targeting moiety which binds to the surface of a mammalian cell, linked to a polypeptide cytotoxic agent. Preferably, the targeting moiety is a cytokine or single chain variable region polypeptide derived from an antibody which does not bind to a receptor expressed on normal pluripotent bone marrow progenitor cells. If the targeting moiety is a cytokine, it is preferred that it be GM-CSF, IL-2, IL-3, IL-4, IL-6, IL-7, IL-8, IL-9, IL-10, IL-12, EGF, FGF, PDGF, or NGF. If the targeting moiety is a single chain variable region polypeptide, it is preferred that it be directed against the CD2, CD3, CD4, CD5, CD7, CD13, CD19, CD22, CD24, CD33, CD40, CD45, CD72, TXU.1, NXU.1, TP-1, or TP-3 antigen. More preferably, the single chain variable region polypeptide is the Fab fragment, e.g., of antibody B43. It is preferred that the cytotoxic agent of the present invention is a bacterial or plant toxin. Most preferably, the cytotoxic agent is recombinant PAP or a bioactive mutant or variant thereof. Most preferably, the cytotoxic agent is recombinant PAP comprising an amino acid sequence according to SEQ ID NO:2, SEQ ID NO:3, SEQ ID NO:4, SEQ ID NO:5, SEQ ID NO:6, SEQ ID NO:7, SEQ ID NO:8, or a biologically functional equivalent thereof. Furthermore, it is further preferred that the mammalian cell be a cancer cell or cell on the surface of a tumor blood vessel. Most preferably, the cell will be associated with leukemia, lymphoma, a brain tumor, neuroblastoma, osteosarcoma, soft tissue sarcoma, breast cancer, prostate cancer, ovarian cancer, testicular cancer, melanoma, lung cancer, or colon cancer.

In another embodiment, the present invention provides an immunotoxin for the treatment of AIDS. In this embodiment of the invention, it is preferred that the targeting moiety be a monoclonal antibody, monoclonal antibody fragment, or antibody-derived single chain variable region polypeptide that binds to the surface of T-cells or monocytes or macrophages. Most preferably, the targeting moiety will be a monoclonal antibody, monoclonal antibody fragment, or single chain variable region polypeptide directed against the CD2, CD3, CD4, CD5, CD7, CD14 or TXU.1 antigen.

It is preferred that the cytotoxic agent of the present invention is a bacterial or plant toxin. More preferably, the cytotoxic agent is recombinant pokeweed antiviral protein (PAP) or a bioactive mutant or variant thereof. Most preferably, the cytotoxic agent is recombinant PAP comprising an amino acid sequence according to SEQ ID NO:2, SEQ ID NO:3, SEQ ID NO:4, SEQ ID NO:5, SEQ ID NO:6, SEQ ID NO:7, SEQ ID NO:8, or a biologically functional equivalent thereof. Based on our preclinical data with wild-type PAP in mouse models of human AIDS, such immunotoxins can be efficacious in the treatment of human AIDS.

In another embodiment, the present invention provides a fusion toxin for the treatment of AIDS. In this embodiment of the invention, it is preferred that the targeting moiety be a cytokine that binds to the surface of T-cells or monocytes or macrophages. Most preferably, the targeting moiety will be M-CSF, GM-CSF, IL-2, IL-3, IL-4, IL-6, IL-7, IL-8, IL-9, IL-10, or IL-12. It is preferred that the cytotoxic agent of this embodiment of the present invention is a bacterial or plant toxin. More preferably, the cytotoxic agent is recombinant pokeweed antiviral protein (PAP) or a bioactive mutant or variant thereof. Most preferably, the cytotoxic agent is recombinant PAP -comprising an amino acid sequence according to SEQ ID NO:2, SEQ ID NO:3, SEQ ID NO:4, SEQ ID NO:5, SEQ ID NO:6, SEQ ID NO:7, SEQ ID NO:8, or a biologically functional equivalent thereof. Based on our preclinical data with wild-type PAP in mouse models of human AIDS, such fusion toxins can be efficacious in the treatment of human AIDS.

The present invention also includes a process for preparing an immunotoxin useful for the treatment of cancer or AIDS. Specifically, the process comprises of the steps of preparing the recombinant PAP by (i) cloning a DNA sequence that encodes PAP or a PAP functionally equivalent mutant or variant into an expression vector; (ii) transforming *E. coli* cells or other host cells with the expression vector; (iii) maintaining the transformed cells under biologic conditions sufficient for expression of PAP or the PAP equivalent.

Once the recombinant PAP has been isolated, a suitable targeting moiety is provided such as a monoclonal antibody, monoclonal antibody fragment, or a single chain variable region polypeptide in purified form. The recombinant PAP or PAP equivalent is then linked to the targeting moiety by methods of conjugation well known to those of skill in the art. For example, one such method is the utilization of a heterobifunctional crosslinker, e.g. SPDP. Finally, the immunotoxin is purified by size exclusion and affinity chromatography and any endotoxin is removed.

Also provided in the present invention is a process for preparing a fusion toxin, i.e., for the treatment of cancer or AIDS. Specifically, the process comprises of the steps of constructing an expression vector comprising DNA encoding a fusion protein comprising recombinant PAP- binding polypeptide, such as a recombinant cytokine or recombinant PAP-single chain variable region polypeptide expression vector. The vector is utilized in the transformation of host cells such as *E. coli* cells. The transformed cells are then maintained under biologic conditions sufficient for expression of the fusion toxin. Once the fusion toxin has been expressed, it can be isolated and purified by size exclusion and affinity chromatography steps, and any endotoxin can be removed.

The present invention also provides a therapeutic method for the treatment of preselected cancers. The method comprises parenterally administering to a patient who is afflicted with a target cancer an effective amount of a pharmaceutical composition comprising an immunotoxin of the present invention. As used herein, the phrase "preselected cancer" refers to diseases associated with the proliferation of mammalian cells expressing the antigens listed above, recognized by the targeting moieties of the present invention. Such cancers include, but are not limited to, B-lineage acute lymphoblastic leukemia, chronic lymphocytic leukemia, B-lineage lymphoma, blast crisis of chronic myelocytic leukemia, hairy cell leukemia, AIDS lymphoma, EBV-lymphoma, brain tumors, neuroblastoma, osteosarcoma, soft tissue sarcoma, breast cancer, prostate cancer, ovarian cancer, testicular cancer, melanoma, lung cancer, or colon cancer.

Further provided is a therapeutic method for treating preselected cancers which comprises parenterally administering to a patient who is afflicted with a target cancer an effective amount of a pharmaceutical composition comprising a fusion toxin of the present invention. As used herein, the phrase "preselected cancer" refers to diseases associated with the proliferation of mammalian cells expressing the receptor recognized by the targeting moieties listed above. Such target cancers include, but are not limited to, acute or chronic myelogenous leukemia, mixed lineage leukemia, breast cancer, colon cancer, prostate cancer, lung cancer and T-cell leukemia, B-lineage acute lymphoblastic leukemia, chronic lymphocytic leukemia, B-lineage lymphoma, blast crisis of chronic myelocytic leukemia, hairy cell leukemia, AIDS lymphoma, EBV-lymphoma, brain tumors, neuroblastoma, osteosarcoma, soft tissue sarcoma, ovarian cancer, testicular cancer or melanoma.

The isolation of PAP mutants or variants that are nontoxic to yeast and have potent antiviral activity against TMV indicate that the ribosome inhibitory activity of PAP can be dissociated from its antiviral activity. It is believed that the anti-viral, i.e., anti-HIV activity of PAP is not diminished when it is mutated and has lost its RIP activity. It is thus expected that the biotherapeutic agents of the present invention will provide the basis for a highly effective procedure to inhibit HIV replication in mammalian monocytes and/or T-cells; thereby, providing a method to treat patients with HIV-infection, ARC or AIDS. It is further expected that the biotherapeutic agents of the present invention will provide the basis for an effective method to inhibit other retroviruses (HTLV-1, etc.) and viruses other than retroviruses including, but not limited to, members of the herpes virus group (HSV, CMV, EBV), influenza viruses, rhinoviruses, papovaviruses (human papilloma), adenoviruses, hepatitis virus, and the like.

DETAILED DESCRIPTION OF THE INVENTION

I. Biotherapeutic Agents

A. Immunotoxins

Several requirements must be fulfilled for an immunotoxin to be effective. Pastan et al., *Cell,* 47, 641 (1986). First of all, the immunoconjugates should be specific and should not react with normal tissues. Binding to tissues that do not express antigen can be reduced by removal of the nonspecific natural cell-binding subunits or domains of the toxin. Furthermore, because plant glycoprotein toxins contain mannose oligosaccharides that bind to cells of the reticuloendothelial system and, in some cases, also contain fucose residues that are recognized by the receptors on hepatocytes, deglycosylation of plant toxins may be required to avoid rapid clearance and potential cytotoxic effects on these cells. Secondly, the linkage of the toxin to the antibody should not impair the capacity of the antibody to bind to the antigen. Third, the immunotoxin must be internalized into the endosomic vesicles. Thus, toxins directed by monoclonal antibodies to surface receptors that are normally internalized may be more active than those directed toward noninternalizing cell surface molecules. Fourth, the active component of the toxin must translocate into the cytoplasm. Finally, for in vivo therapy, the linkage must be sufficiently stable to remain intact while the immunotoxin passes through the tissues of the patient to its cellular site of action. The first generation of heterobifunctional cross-linkers used to bind the toxin to the monoclonal antibody generated disulfide bonds that were unstable in vivo. This problem was solved in part by the synthesis of more stable cross-linkers, which used phenyl or methyl groups, or both, adjacent to the disulfide bond to restrict access to the bond. These various goals can be in conflict; for example, the removal of the B chain of ricin reduces nonspecific binding but also reduces the capacity of the residual A-chain monoclonal antibody conjugate to translocate across the endosomic vesicle membrane.

The activity of an immunotoxin is initially assess by measuring its ability to kill cells with target antigens on their surfaces. Because toxins act within the cells, receptors and other surface proteins that naturally enter cells by endocytosis usually make good targets for immunotoxins, but surface proteins that are fixed on the cell surface do not. However, if several antibodies recognizing different epitopes on the same cell surface protein are available, it is useful to test them all. This is because some, perhaps by producing a conformational change in the target proteins' structure, may induce its internalization or direct its intracellular routing to an appropriate location for toxin translocation. May et al., *Cell Immunol.,* 135, 490 (1991). Also, it is possible to induce internalization of a target surface protein if the immunotoxin contains a form of a toxin in which the binding of the toxin moiety to its receptor, although weakened by chemical modification, still occurs and promotes internalization since toxin receptors are efficiently internalized. Willingham et al., *Proc. Natl. Acad. Sci. USA,* 84, 2474 (1987).

Several immunotoxins have been developed and approved for human trials. Two different kinds of trials have been conducted. The first involves the ex vivo addition of immunotoxins to harvested bone marrow to eliminate containing tumor cells before reinfusion in patients undergoing autologous bone marrow transplantation. A variety of antibodies, linked to ricin or ricin A chain, including anti-CD5 and anti-CD7, have been used for this purpose. Uckun et al., *Blood,* 76, 1723 (1990). The second kind of trial involves the parenteral administration of immunotoxins, either regionally (such as to the peritoneal cavity) or systemically, to patients with cancer. These have been primarily Phase 1 and 2 trials in patients in which conventional treatments have failed, and the patients have a large tumor burden. So far, the antibodies used for the preparation of immunotoxins to treat carcinomas or other solid tumors have been found to react with important normal human tissues (such as neural tissue and bone marrow) and produce dose-limiting toxicity without significant clinical responses. See, for example, Gould et al., *J. Natl. Cancer Inst.,* 81 775 (1989).

B. Fusion proteins

Fusion proteins are hybrid cytotoxic proteins made by recombinant DNA technology that are designed to selectively kill cancer cells. Fusion proteins are synthesized by the fusion of a targeting moiety that binds to a receptor on a mammalian cell to a cytotoxic agent. The cytotoxic agent is preferably a portion of a bacterial or plant toxin. The activity of these fusion proteins depends not only on the toxin utilized, but also on efficient binding of antibody to antigen, endocytosis, and intracellular release of functional ribosome inactivating proteins.

C. Targeting Moieties

Since it is established that many cancer cells overproduce cytokine receptors, the targets for this type of therapy can be growth factor receptors, differentiation antigens, or other less characterized cell surface antigens. Thus, effective targeting moieties include, but are not limited to, cytokines, cytokine subunits, antibodies or antibody subunits. Specifically, as used herein the term "targeting moiety" is defined to mean all monoclonal antibodies, monoclonal antibody fragments, single chain variable region polypeptides, and cytokines used in the production of immunotoxins and fusion toxins. Useful examples of targeting moieties include, but are not limited to, a monoclonal antibody, monoclonal antibody fragment, or single chain variable region polypeptide directed against the CD2, CD3, CD4, CD5, CD7, CD 13, CD 14, CD 19, CD22, CD24, CD33, CD40, CD45, CD72, TXU.1, NXU.1, TP-1, or TP-3 antigen. Furthermore, the targeting moiety of the present invention may be a cytokine. If the targeting moiety is a cytokine, preferred cytokines include, but are not limited to, GM-CSF, IL-2, IL-3, IL-4, IL-6, IL-7, IL-8, IL-9, IL-10, IL-12, EGF, FGF, PDGF, or NGF.

1. Antibodies

Monoclonal antibodies (MoAbs) are produced by the fusion of spleen lymphocytes with malignant cells (myelomas) of bone marrow primary tumors. Milstein, *Sci. Am.,* 243, 66 (1980). The procedure yields a hybrid cell line, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and yield monoclonal antibodies in extremely high concentration.

Monoclonal antibodies have largely been applied clinically to the diagnosis and therapy of cancer and the modulation of the immune response to produce immunosuppression for treatment of autoimmune and graft versus host diseases (GVHD) and for prevention of allograft rejection. Human monoclonal antibodies have also been applied clinically against cytomegalovirus, *Varicella zoster* virus, and the various specific serotypes of *Pseudomonas aeruginosa, Escherichia coli,* and *Klebsiella pneumoniae.*

Antibodies and their fragments can also be genetically engineered to have more rapid clearance. This is desirable when a monoclonal antibody is conjugated to a radionucleotide for use in radioimmunoscanning. For example, antigen-binding fragment (Fab), $F(ab')_2$, or single chain Fv fragments of monoclonal antibodies have survival half lives of less than 5 hours. Rapid turnover can also be accomplished by the deletion of the $CH_2$ domain as demonstrated for an antibody reactive with the disaloganglioside GD2 expressed on human tumors of neuroectodermal origin. Müeller et al., *Proc. Natl. Acad. Sci. USA,* 87, 5702 (1990).

Furthermore, due to their large size, intact antibodies and the corresponding antibody-toxin conjugates are restricted in their ability to migrate from the vascular regions, are heterogenous as immunoconjugates (which can result in linkage of several toxin molecules to one immunoglobulin molecule), and their production is expensive and very labor intensive. See, for example, U.S. Pat. No. 4,831,117 to Uckun and U.S. Pat. No. 4,671,958 to Rodwell et al., the teachings of which are herein incorporated by reference. Again, genetic engineering has been used for the expression of the light and heavy chain variable regions of antibodies in bacteria as single chain Fv (scFv) fragments in an attempt to improve on the efficacy of antibodies and their corresponding immunoconjugates. Pastan et al., *Science,* 254, 1173 (1991). In general, these molecules have been insoluble and need to be denatured and refolded before binding activity can be detected. One problem with production of antibody binding domains in this manner is that high affinity antibody binding cannot be successfully reconstituted in all instances. The parameters that govern the ability of an antibody to yield scFv that can bind to its target are unknown, thus necessitating the direct cloning and analysis of the candidate antibody gene segments.

a. B43

B43 is a murine IgG1, α monoclonal antibody (MoAb) recognizing a 95 kDa target B lineage restricted phosphoglycoprotein, which is identified as the CD19 antigen according to the World Health Organization (WHO) established CD (cluster of differentiation) nomenclature. The chemical, immunological and biological features of B43 MoAb have been described in detail in previously published reports. Uckun et al., *Blood,* 71, 13 (1988).

CD19 antigen is a B-lineage specific surface receptor which is expressed on malignant cells from 85% of patients with acute lymphoblastic leukemia (ALL). Uckun et al., *Blood,* 71, 13 (1988). CD19 is found on the surface of each B-lineage lymphoma cell and B-lineage cell at a high density (>1,000,000 molecules/cell and >50,000 molecules/cell, respectively) but is absent from the parenchymal cells of life-maintaining nonhematopoietic organs, as well as from blood related myeloid and erythroid cells, T-cells and bone marrow stem cells, reducing the opportunity for non-specific toxicity when anti-CD19 antibodies are used in biotherapy. Uckun et al., *J. Exp. Med.* 163, 347 (1986). This B-lineage specific antigen shows a high affinity for the B43 (anti-CD19) monoclonal antibody ($Ka>10^8 M^{-1}$), undergoes antibody induced internalization upon binding of B43 and is not shed from the cell surface. Uckun et al., *J. Exp. Med.* 163, 347 (1986). $CD19^+$ acute lymphoblastic leukemias are believed to originate from putative developmental lesions in normal B-cell precursor clones during early phases of ontogeny and are therefore classified as B-lineage leukemia F. M. Uckun, *Blood,* 76, 1908 (1990).

b. TP-1/TP-3

Monoclonal antibodies TP-1 and TP-3 have been shown to react with different epitopes of an 80 kd antigen on human and canine osteosarcoma which is referred to as the p80 antigen. Bruland et al., "New monoclonal antibodies specific for human sarcomas", *Int. J. Cancer,* 38, 27 (1986). Specifically, TP-3 is an $IgG_{2b}$ monoclonal antibody which recognizes mesenchymal tumors including osteosarcomas as well as the budding capillaries of a wide variety of tumors. Ø. Bruland et al., *Cancer Research,* 48, 5302 (1988). TP-1 and TP-3 also bind a variety of other human sarcomas including hemangiopericytoma, chondrosarcoma, malignant fibrous histiocytoma (MFH), and synovial cell sarcoma. Bruland et al., "Expression and characteristics of a novel human osteosarcoma-associated cell surface antigen", *Cancer Research,* 48, 5302 (1988).

The distribution of the TP-1/TP-3 antigen on normal tissues is very limited. This limited tissue distribution that makes the TP-3 antigen an attractive choice for immunotoxin therapy. The current state of knowledge of distribution of the TP-1/TP-3 antigen on normal tissues and mesenchymal tumors has been recently summarized by Bruland and Phil. "Immunoscintigraphy and radioimmunotherapy: Useful approaches in the management of osteogenic sarcoma" In: *Frontiers of Osteosarcoma Research,* J. F. Novak and J. H. McMaster (eds.), Hogrefe and Huber Publishers, pp. 149–159, (1993). Negative tissues included fibroblasts, peripheral blood cells, cells in the marrow, fetal skin fibroblasts, fetal lung fibroblasts, amniocytes, fibrous connective tissue, skeletal muscle, cartilage, synovia, peripheral nerve, tonsil, spleen, liver, colon, and lung. Only newly active bone callus, placental endothelial cells, proximal tubule of kidney (weak binding), and occasional cells in the adrenal medulla were positive for TP-1 and TP-3 binding. Bruland et al., *Cancer Research,* 48, 5302 (1988).

2. Cytokines a. Granulocyte-Macrophage Colony-Stimulating Factor (GMCSF)

Native GMCSF is a glycosylated protein with an amino acid length of 127 residues and a molecular weight of 14–28 kd. The gene that encodes GMCSF in humans is found on the long arm of chromosome 5, linked in tandem to the IL-3 gene, and mapping closely to the genes for other hematopoietic cytokines (including IL-4 and IL-5) and their receptors. Cannistern et al., *J. Biol. Chem.* 265, 12656 (1990); Van Leeuwen et al., *Blood,* 73, 1142 (1989). The native and recombinant forms of GMCSF stimulate the proliferation, differentiation and function of myeloid lineage progenitor cells, and enhance the functional activation of granulocytes, monocytes, and macrophages. Gasson, *Blood,* 77, 1131 (1991); Seif et al., *Science,* 230, 872 (1985). Furthermore, a defective regulation of expression of the genes for individual cytokines or their receptors (e.g., GMCSF and GMCSF-R), which causes a pathological autocrine or paracrine stimulation of leukemic cell growth, has been implicated in the leukemogenesis of AML. Rogers et al., *Exp. Hematol.,* 2, 593 (1994). It has been reported that leukemic cells from approximately two-thirds of patients with AML show an autonomous growth pattern because of autocrine GMCSF production and secretion. Rogers et al., cited supra; Young and Griffin, *Blood,* 68, 1178 (1986).

The biological effects of GMCSF are species-specific and mediated through the activation of a specific receptor. The heterodimeric high affinity GMCSF-R is composed of an α-chain specific for GMCSF and a β-chain that can also associate with the interleukin 3 and interleukin 5 receptor α-chains. Kastelein et al., *Oncogene,* 8, 231 (1993). Reflecting a common molecular theme among many cytokine receptors, the functional high affinity GMCSF receptor shares a common β subunit with the IL-3 and IL-5 receptors, and explaining the partial overlap in biological effects of GMCSF and IL-3. The high affinity GMCSF-R is expressed at high levels on myeloid leukemia cells and may provide an appropriate target for biotherapy of AML, since it is not expressed on the surface of pluripotent lymphohematopoietic stem cell populations. Higashigawa et al., *Leuk. Res.,* 16, 1049 (1992).

b. Interleukin 3 (IL-3)

IL-3, also known as multi-colony-stimulating factor (multi-CSF), is a glycosylated protein with an amino acid length of 133 amino acid residues and native molecular weight of 15 to 30 kDa in humans. Yang et al., *Cell,* 47, 3 (1986); Lee et al., *Nature,* 289, 407 (1981). Its gene is located on the 5q23-13 region on long arm of chromosome 5, in relatively close proximity to the GMCSF gene, and linked to other cytokine genes including IL-4 and IL-5. Human IL-3 is active in primates, however, it demonstrates species specificity in that it is not active in rodents. The biological effects of IL-3 in humans are mediated through a high affinity receptor that is composed of a β chain that is shared with the GMCSF and IL-5 receptors, and an α-chain that is apparently specific for IL-3. Although the α-chain alone may bind IL-3 with relatively low affinity, the β chain alone does not bind the cytokine, and both the α and β chain together are required for high affinity binding and signal transduction. IL-3 stimulates proliferation in progenitors at a somewhat earlier stage than GMCSF, but also does not stimulate the pluripotent primitive hematopoietic stem cell. IL-3 also stimulates colony formation and differentiation in committed progenitors in granulocytic, macrophage, mast cell, megakaryocytic and erythroid lineages.

D. Cytotoxic Agents

The limited efficacy of many unmodified monoclonal antibodies has led to an alternative approach, that is, the use of these agents as carriers of cytotoxic agents. An array of toxins of bacterial and plant origin have been coupled to monoclonal antibodies for production of immunotoxins. The strategy is to select from nature a cytotoxic protein and then to modify the cytotoxic protein so that it will no longer indiscriminately bind and kill normal cells, but will instead kill only the cells expressing the antigen identified by the monoclonal antibody. To be optimally effective, such an approach requires that internalization of relatively small numbers of cytotoxic molecules be lethal to target cells, as there are limited receptor sites on the cell surface. The cytotoxic agents produced by certain bacteria and plants that inactivate cellular protein synthesis meet this criteria as, unlike most chemotherapeutic agents which act in a stoichiometric manner, they are catalytic in their lethal activity. In general, less than ten toxin molecules in the cytoplasm are sufficient to kill the cell.

Two classes of cytotoxic agents that inactivate protein synthesis have been widely employed in the construction of biotherapeutic agents. Diphtheria toxin (DT) and *Pseudomonas aeruginasa* exotoxin A represent one class of these toxins, and kill cells by catalyzing the ADP-ribosylation and inactivation of elongation factor 2, an essential cofactor in protein synthesis.

Lethally inhibiting protein synthesis in a complementary manner, members of the other class of toxins covalently modify the ribosome such that it can no longer productively interact with elongation factor 2. This latter family of toxins includes pokeweed antiviral protein (PAP), ricin, abrin, gelonin, saporin, and alpha-sarcin. The ribosome inactivating proteins derived from plants consist of either two chains, including a binding chain and catalytic chain (e.g. ricin), or a single catalytic chain alone (e.g. PAP or saporin).

1. PAP

PAP is a member of the hemitoxin group of toxins and thus inactivates ribosomes by the specific removal of a single adenine from the conserved loop sequence found near the 3' terminus of all larger rRNAs. Irvin et al., *Pharmacology and Therapeutics,* 55, 279, (1992). This specific depurination greatly reduces the capability of elongation factors to interact with ribosomes and results in an irreversible shut-down of protein synthesis. Irvin et al., cited supra. Furthermore, PAP is one of the most active ribosomal inactivating proteins. In a comparison of cytotoxicity of anti-mouse IgG immunotoxins gelonin, ricin A chain, momordin, dianthin 32, saporin, and PAP, the PAP constructs were among the most potent inmmunotoxins tested. Irvin et al., cited supra. Bolognesi et al., "A comparison of anti-lymphocyte immunotoxins containing different ribosome-inactivating proteins and antibodies", *Clin. Exp. Immunol.,* 89, 341 (1992).

a. Wild-type PAP

There are three subtypes of pokeweed antiviral protein (PAP) the expression of which are dependent upon the season. PAP is found in spring leaves of pokeweed (*Phytolacca americana*), PAP II is found in late summer leaves, and PAP-S is found in seeds. Irvin, *Pharmacol. Ther.,* 21, 371 (1983). Small differences exist in their sizes (all are approximately 29,000 MW) and there are only small differences, if any, between their ability to inhibit ribosomes catalytically. Houston et al., "Immunotoxins made with Toxins and Hemitoxins other than Ricin", in *Immunological Antibody Conjugates in Radioimaging and Therapy of Cancer,* C. W. Vogel, ed., New York, Oxford University Press, P. 71 (1987). "Wild-type PAP" is defined herein to mean the PAP amino acid sequence 1–262 (SEQ ID NO:1), the 22-amino acid N-terminal signal peptide, and the 29 amino acid C-terminal extension (amino acids enumerated 263–291; illustrated in Table 1, below. Thus, by "wild-type, mature PAP", it is meant that the amino acid sequence corresponds essentially to the PAP amino acid sequence 1–262 shown in Table 1.

TABLE I

```
                                                            (SEQ ID NO: 1)
CTATGAAGTCGGGTCAAAGCATATACAGGCTATGCATTGTTAGAAACATTGATGCCTCTGATCC
CGATAAACAATACAAATTAGACAATAAGATGACATACAAGTACCTAAACTGTGTATGGGGGAG
TGAAACCTCAGCTGCTAAAAAACGTTGTAAGAAAAAAAGAAAGTTGTGAGTTAACTACAGGG
CGAAAGTATTGGAACT

                  (1)
AGCTAGTAGGAAGGGAAG ATG AAG TCG ATG CTT GTG GTG ACA ATA TCA ATA TGG CTC
                   Met Lys Ser Met Leu Val Val Thr Ile Ser Ile Trp Leu

                                      (67)
ATT CTT GCA CCA ACT TCA ACT TGG GCT GTG AAT ACA ATC ATC TAC AAT GTT GGA AGT
```

TABLE I-continued

```
Ile Leu Ala Pro Thr Ser Thr Trp Ala Val Asn Thr Ile Ile Tyr Asn Val Gly Ser
                                    (1)
                                  (10)

   (100)
ACC ACC ATT AGC AAA TAC GCC ACT TTT CTG AAT GAT CTT CGT AAT GAA GCG AAA
Thr Thr Ile Ser Lys Tyr Ala Thr Phe Leu Asn Asp Leu Arg Asn Glu Ala Lys
                                     (20)

GAT CCA AGT TTA AAA TGC TAT GGA ATA CCA ATG CTG CCC AAT ACA AAT ACA AAT
Asp Pro Scr Leu Lys Cys Tyr Gly Ile Pro Met Leu Pro Asn Thr Asn Thr Asn
   (30)                                    (40)

CCA AAG TAC GTG TTG GTT GAG CTC CAA GGT TCA AAT AAA AAA ACC ATC ACA CTA
Pro Lys Tyr Val Leu Val Glu Leu Gln Gly Ser Asn Lys Lys Thr Ile Thr Leu
           (50)                                    (60)

ATG CTG AGA CGA AAC AAT TTG TAT GTG ATG GGT TAT TCT GAT CCC TTT GAA ACC
Met Leu Arg Arg Asn Asn Leu Tyr Val Met Gly Tyr Ser Asp Pro Phe Glu Thr
                   (70)                                    (80)

AAT AAA TGT CGT TAC CAT ATC TTT AAT GAT ATC TCA GGT ACT GAA CGC CAA GAT
Asn Lys Cys Arg Tyr His Ile Phe Asn Asp Ile Ser Gly Thr Glu Arg Gln Asp
                           (90)                                    (100)

GTA GAG ACT ACT CTT TGC CCA AAT GCC AAT TCT CGT GTT AGT AAA AAC ATA AAC TTT
Val Glu Thr Thr Leu Cys Pro Asn Ala Asn Ser Arg Val Ser Lys Asn Ile Asn Phe
                                   (110)

GAT AGT CGA TAT CCA ACA TTG GAA TCA AAA GCG GGA GTA AAA TCA AGA AGT CAG
Asp Ser Arg Tyr Pro Thr Leu Glu Ser Lys Ala Gly Val Lys Ser Arg Ser Gln
(120)                                  (130)

GTC CAA CTG GGA ATT CAA ATA CTC GAC AGT AAT ATT GGA AAG ATT TCT GGA GTG
Val Gln Leu Gly Ile Gln Ile Leu Asp Ser Asn Ile Gly Lys Ile Ser Gly Val
       (140)                                   (150)

ATG TCA TTC ACT GAG AAA ACC GAA GCC GAA TTC CTA TTG GTA GCC ATA CAA ATG
Met Ser Phe Thr Glu Lys Thr Glu Ala Glu Phe Leu Leu Val Ala Ile Gln Met
               (160)                                       (170)

GTA TCA GAG GCA GCA AGA TTC AAG TAC ATA GAG AAT CAG GTG AAA ACT AAT TTT
Val Ser Glu Ala Ala Arg Phe Lys Tyr Ile Gku Asn Gln Val Lys Thr Asn Phe
                       (180)                                       (190)

AAC AGA GCA TTC AAC CCT AAT CCC AAA GTA CTT AAT TTG CAA GAG ACA TGG GGT
Asn Arg Ala Phe Asn Pro Asn Pro Lys Val Leu Asn Leu Gln Glu Thr Trp Gly
                              (200)

AAG ATT TCA ACA GCA ATT CAT GAT GCC AAG AAT GGA GTT TTA CCC AAA CCT CTC
Lys Ile Ser Thr Ala Ile His Asp Ala Lys Asn Gly Val Leu Pro Lys Pro Leu
(210)                                  (220)

GAG CTA GTG GAT GCC AGT GGT GCC AAG TGG ATA GTG TTG AGA GTG GAT GAA ATC
Glu Leu Val Asp Ala Ser Gly Ala Lys Trp Ile Val Leu Arg Val Asp Glu Ile
       (230)                                  (240)

AAG CCT GAT GTA GCA CTC TTA AAC TAC GTT GCT GGG AGC TGT CAG ACA ACT TAT
Lys Pro Asp Val Ala Leu Leu Asn Tyr Val Gly Gly Ser Cys Gln Thr Thr Tyr
               (250)                                   (260)    (262)

AAC CAA AAT GCC ATG TTT CCT CAA CTT ATA ATG TCT ACT TAT TAT AAT TAC ATG GTT
Asn Gln Asn Ala Met Phe Pro Gln Leu Ile Met Ser Thr Tyr Tyr Asn Tyr Met Val
                       (270)                                       (280)

                                  (939)
AAT CTT GGT GAT CTA TTT GAA GGA TTC TGA TCA TAA ACA TAA TAA GGA GTA TAT ATA
Asn Leu Gly Asp Leu Phe Glu Gly Phe
                           (290)

TAT TAC TCC AAC TAT ATT ATA AAG CTT AAA TAA GAG GCC GTG TTA ATT AGT ACT TGT

TGC CTT TTG CTT TAT GGT GTT GTT TAT TAT GCC TTG TAT GCT TGT AAT ATT ATC TAG

AGA ACA AGA TGT ACT GTG TAA TAG TCT TGT TTG AAA TAA AAC TTCCAA TTA TGA TGC

AAA AAA AAA AAA AAA
```

b. Mutant/Variant PAP (PAP-v)

The amino acid sequence of PAP-v differs from that of wild-type PAP in terms of a Leu20Arg (i.e., an arginine residue at position 20 of mature PAP as opposed to a leucine residue) and a Tyr49His substitution. Upon expression in eukaryotic cells, the N-terminal 22-amino acid sequence is co-translationally cleaved, yielding a polypeptide having a molecular weight of about 32 kDa, which is then further processed by the cleavage of the C-terminal 29-amino acids, yielding mature, wild-type PAP (hereinafter "PAP (1–262)") (i.e., that which is isolated from *Phytolacca americana* leaves), having a molecular weight of about 29 kDa. See Irvin et al., *Pharmac. Ther.,* 55, 279 (1992). The PAP mutants of the present invention exhibit reduced phytocytoxicity and enhanced antiviral activity compared to PAP and PAP-v (variant PAP).

The PAP mutants of the present invention can be characterized generally as (1) those which exhibit altered compartmentalization in vivo; and (2) C-terminal mutants including, but not limited to, deletion or frameshift mutants. The first category of PAP mutants have altered compartmentalization properties in vivo; that is, they are not localized in the same subcellular compartment as wild-type PAP. It is believed that these PAP mutants are unable to undergo co-translational processing (to remove the 22 amino acid signal peptide) and/or post-translational processing (to remove the 29-amino acid C-terminal fragment) which results in substantially diminished or negligible phytotoxicity. What is particularly surprising or unexpected about the function of these mutant PAPs in vivo is that the mutations are located within the sequence encoding mature PAP (1–262), and not within the signal peptide or the 29-amino acid C-terminal extension. In addition, the mutant PAPs are enzymatically active in vitro, indicating that toxicity in vivo is not solely a function of enzymatic activity. Preferred PAP mutants include a conservative point mutation such that wild-type PAP amino acid residue 75 glycine (Gly75) is changed to valine HMNT123-1), alanine, isoleucine, or leucine (SEQ ID NO:5), or (2) a conservative or non-conservative point mutation at wild-type PAP amino acid residue 97 glutamic acid (Glu97) is changed to lysine HMNT124-1). More preferred PAP mutants are PAP (1–262, Gly75Val; SEQ ID NO:2) and PAP (1-262, Glu97Lys; SEQ ID NO:6), the respective DNAs of which can be prepared by changing the wild-type GGT codon for glycine75 to GTT (valine), and GAA codon for glutamic acid 97 to AAA (lysine). The PAP mutants of the present invention may further include the N-terminal 22-amino acid signal peptide of wild-type PAP (SEQ ID NO:7) and/or the 29 amino acid C-terminal extension (SEQ ID NO:8), both of which are shown in Table 1, above. Other PAP mutants having altered compartmentalization properties can be identified by the selection method described below.

The second category of PAP mutants of the present invention have deletions or amino acid substitutions in the C-terminal region of PAP. It has been discovered that these mutants are unexpectedly non-toxic in vivo even though they are enzymatically active in vitro. Preferred mutants have deletions of from 25 to 76 amino acids of mature PAP, and more preferred are PAP (1–236)-PAP (1–184), inclusive. Deletions shorter than about 26 or longer than about 76 mature PAP amino acids are included in the scope of the present invention provided that they exhibit anti-viral activity. It is believed that the sequence of PAP amino acids 244Glu-259Cys (shown in Table 1), which is homologous to the consensus for the prokaryotic membrane lipoprotein lipid attachment (See Hayashi et al., *J. Bioeng. Biomem.,* 22,451 (1990)), and which is absent from each of the PAP mutants disclosed above, is involved in binding of PAP to phospholipids on endoplasmic reticulum (ER) membranes, which facilitates the translocation of PAP into the cytosol of the cell where it inhibits protein synthesis. Disarming this function, e.g., by deletion, point or frameshift mutation, will result in a PAP mutant with a better therapeutic index by having less cytotoxicity but full antiviral activity. The PAP mutants can be further modified by way of point mutations, additions and deletions provided that the resultant PAP mutant retains the properties of reduced cytotoxicity and full antiviral activity. For example, the N-terminus may be changed to a methionine residue, either by substitution or addition, to allow for expression of a DNA encoding the mutant PAP in various host cells, particularly *E. coli.* DNA encoding the mutant PAPs of the present invention can be prepared by mutagenesis of known PAP genes. See Ausubel et al., (eds.), Vol. 1, Ch. 8 in *Current Protocols in Molecular Biology,* Wiley N.Y. (1990). The DNA may also be prepared via PCR techniques. See *PCR Protocols,* Innis et al. (eds.), Academic Press San Diego, Calif. (1990).

c. Anti-viral activity of Pokeweed Antiviral Protein

PAP displays broad-spectrum antiviral activity against plant viruses, herpes simplex virus, cytomegalovirus, poliovirus, and influenza virus. Aron et al., *Agents Chemotherapy,* 17, 1032 (1980). In fact, pokeweed antiviral protein was discovered due to its ability to inhibit the transmission of tobacco mosaic virus (TMV) in plants and it was subsequently demonstrated that the purified protein was equally effective against a number of other plant viruses. Tomlinson et al., *J. Gen. Virol.,* 22, 225 (1974). All of these experiments were performed in a similar manner; PAP was mixed with the virus inoculum which was then rubbed on plant leaves in the presence of an abrasive substance, such as carborundum, which damages the tissue allowing the entry of the virus and presumably the PAP. Using this method, it was found that highly diluted solutions of PAP were capable of inhibiting local lesion formation caused by southern bean mosaic virus as well as cucumber mosaic virus. Wyatt et al., *Phytopath.,* 59, 1787 (1969); Tomlinson et al., cited supra. Using the local lesion assay system on Phaseolus vulgaris, it has been shown that PAP inhibited viral infection at very low concentrations. Irvin et al., *Arch. Biochem. Biophys.,* 200, 418 (1980). PAP has also been shown to effectively inhibit TWV infection of tobacco protoplasts with nearly complete inhibition obtained with 10 $\mu$g/mL (≈300 nM). Grasso et al., *Phytopath.,* 98, 53 (1980). Furthermore, in a study done to compare the relative antiviral properties of a number of ribosome inactivating proteins (RIPs) including PAP upon the formation of local lesions on *Nicotiana glutinosa* by TMV, it was found that all of the RIPs tested had antiviral activity, but none of the studied RIP's were as effective as PAP. Stevens et al., *Experientia,* 37, 257 (1981).

Investigations directed towards understanding the action of PAP on virus infection of cultured mammalian cells demonstrated that the antiviral protein was an effective inhibitor of both influenza virus and poliovirus multiplication. Tomlinson et al., cited supra; Ussery et al., *Ann. N.Y. Acad. Sci.,* 284,,431 (1977). PAP has been shown to inhibit the infection of both Vero and HeLa cells by herpes simplex virus (HSV) at $\mu$M concentrations. Aron et al., *Antimicrob. Ag. Chemother.,* 17, 1032 (1980). Also reported in this study was an observation that provided evidence which appears to contradict the proposed mechanism of action. It was observed that PAP produced only a 30% inhibition of total protein synthesis in virus infected cells but inhibited virus production greater than 90%. These results raise the possibility that the antiviral action of PAP may not be due to its inactivation of ribosomes, at least in the case of HSV. These studies also showed that HSV DNA synthesis was inhibited approximately 90% in PAP-treated cells but at the same time had no effect on cellular DNA synthesis.

The antiviral activity of PAP can be greatly enhanced and made highly cell selective by conjugation to antibodies specific for cell-surface receptors. One such immunoconjugate containing PAP has been developed and tested by our group against another member of the herpes family, human cytomegalovirus (HCMV). In this study, the antiviral action of PAP was found to be enhanced by chemically coupling it to an antibody. Gehrz et al., "Treatment of human cytomegalovirus (HCMV) with novel antiviral immunoconjugates", in *Progress in Cytomegalovirus Research,* Landin, M. P. Ed., Elsevier Science Publishers BV, Amsterdam, p. 353 (1991). PAP-antibody conjugates were prepared with monoclonal antibodies specific for the low density lipoprotein receptor (LDLr) and the HCMV envelope glycoprotein gp55, which is expressed on HCMV infected cells, and tested for antiviral effects. The conjugate prepared with PAP and anti-LDLr increased the antiviral action of PAP 1000-fold, resulting in 50% reduction in plaque formation at 1 ng/mL. Conjugation of PAP to anti-gp55 did not increase the antiviral activity observed for PAP alone. Gehrz et al., cited supra. These studies show that the antiviral activity of PAP can be significantly increased by conjugation to cell surface directed antibodies but that the antibodies must be targeted to cell surface proteins that are capable of being internalized.

(1) Anti-HIV activity of PAP

It has been shown that very low concentrations of the RIP trichosanthin inhibit the production of HIV in cells isolated from infected individuals but at the same time do not inhibit total cellular RNA or protein synthesis to a significant degree in the same cells. Teltow et al., *Antimicrob. Ag. Chemother.,* 23, 390 (1983). Partial inhibition of cellular protein and RNA synthesis was observed only at doses which produced the complete inhibition of viral protein p24 production. This observation has been extended to the evaluation of trichosanthin in phase I/II clinical trials as an anti-HIV drug to determine its maximum tolerated dose but its efficacy in treating HIV infection has not been established. Beyer et al., *AIDS,* 4, 1189 (1990). The results obtained from studies on the anti-HIV activity of trichosanthin has stimulated reinvestigations of RIPs and plant materials containing RIPs for anti-HIV activity. In rapid succession a number of proteins were found to have potent anti-HIV activity when tested against infected cell lines. Proteins were isolated from *Momordica charantia, Gelonium multiflorum* seeds, carnation (*Dianthus caryophyllus*) leaves and a 29 kDa protein from the roots of *Triochosanthes kirilowi,* the source of trichosanthin. Lee-Huang et al., *FEBS Lett.,* 272, 12 (1990). All of these proteins inactivated ribosomes at nM concentrations and all exhibited anti-HIV activity with $ID_{50s}$below 0.1 nM. Some of these proteins appear to be proteins which were previously isolated and characterized as RIPs and others may be new isozymes not previously characterized.

PAP has been shown to have anti-HIV and abortifacient properties comparable to those reported for trichosanthin. It has been reported that PAP inhibits HIV-1 production of p24 in both T cells and macrophages infected in vitro with an $ID_{50}$ of approximately $5\times10^3$ pM after treating cells for 4 hours prior to infection. Zarling et al., *Nature,* 347, 92 (1990). These studies also demonstrated that uninfected cells were not adversely affected by PAP treatment at concentrations of up to 30 nM. In a similar study it was shown that PAP-S, added at the time of infection, was more effective than AZT in inhibiting reverse transcriptase activity in isolated mononuclear blood cells infected in vitro with HIV; 0.1 μM PAP inhibited reverse transcriptase by 95 %. PAP-S was found to be nontoxic to uninfected cells at concentrations below 1 μM and addition of PAP-S days later to cells with established infections appeared to be slightly more effective in reducing reverse transcriptase synthesis compared to the results obtained with PAP-S added at the time of infection. Olson et al., *AIDS Res. Human Retroviruses,* 7, 1025 (1991).

Studies have also been conducted to determine whether PAP targeted to CD4+ T cells, by conjugation with MoAbs reactive with normal antigens on CD4+ cells, would be more effective at inhibiting HIV-1 replication. Internalization of PAP-monoclonal antibody conjugates by MoAb receptor-mediated endocytosis results in increased delivery of PAP through the plasma membrane compared to non-specific uptake at high PAP concentrations. Also, PAP immunoconjugates have a plasma half-life of 16–18 hours compared to less than 30 minutes for free PAP, and thus PAP immunoconjugates could have increased therapeutic potential. See Uckun, U.S. patent application Ser. No.07/979,470, now abandoned, which application is incorporated herein by reference. These results demonstrate that PAP targeted to CD4+ T cells by conjugation with a MoAb specific to CD4 is uniquely active at picomolar concentrations. Anti-CD4-PAP is about 1000 times more potent than non-conjugated PAP. Although non-conjugated anti-CD4 can also inhibit HIV-1 replication by binding to the CD4 molecule the receptor for HIV-1 gp120, it was found that inhibition of HIV-1 production occurred only at concentrations of anti-CD4 monoclonal antibody exceeding $7\times10^3$ pM (1 μg/ml). Linsley et al., *J. Virol.,* 62, 3695 (1988).

Also, it was recently reported that at least 1 in 100 CD4+ T cells of HIV-1 infected patients can contain proviral DNA, but the majority of these cells are latently infected and do not produce HIV-1 proteins. Psallidopoulos et al., *J. Virol.,* 63, 4626 (1989); Harper et al., *Proc. Natl. Acad. Sci. USA,* 83, 772 (1986). Whereas expression of CD4 is down regulated by HIV-1 infection of CD4+ T cells in vitro, patients' latently infected cells express CD4. Thus, a study was conducted to investigate whether anti-CD4-PAP would inhibit HIV-1 production in patients' activated CD4+ cells. Hoxie et al., *Science,* 234, 1123 (1986); Schnittman et al., *Science,* 245, 305 (1989). Notably, treatment of patients' anti-CD3-activated T-cells with 5 pM anti-CD4-PAP inhibited production of HIV-1 for at least 22 days, even when the cells were washed free of the conjugate on day 5 and were restimulated with anti-CD3 and IL-2 to induce continued cell proliferation. Zarling et al., cited supra.

In addition, anti-CD4-PAP immunoconjugates were found to effectively reduce viral reverse transcriptase activity in zidovudine resistant infected T-cells. Studies using clinical isolates of zidovudine sensitive and resistant HIV-1 demonstrated that anti-CD4-PAP exhibited potent anti-HIV activity with $IC_{50s}$ below 100 pM for all isolates. Erice et al., *Antimicrob. Ag. Chemother.,* 37, 835 (1993). This study also provided the important observation that the anti-CD4-PAP had no cytotoxic action against the lymphohematopoietic cell populations at concentrations effective against HIV infected T-cells.

Whereby PAP and PAP-monoclonal antibody conjugates inhibit HIV-1 replication, it is unlikely that they inhibit HIV-1 reverse transcriptase in the same manner as 3'-azido- 3'-deoxythymidine (AZT) because PAP also inhibits replication of viruses lacking this enzyme. Ussery et al., *Ann. N.Y. Acad. Sci,* 24, 431 (1977). Furthermore, delaying the onset of treatment of CD4+ T cells with PAP or PAP-immunoconjugates until 24 hours post infection did not decrease the efficacy of the treatment, and thus PAP does not inhibit HIV-1 replication at an early step in infection. Zarling et al., cited supra. PAP also appears not to function by inhibiting HIV-1 release from cells, because it has been found that not only extracellular levels of p24, but also intracellular levels of p24 measured by antigen capture ELISA, were reduced in PAP and anti-CD4-PAP treated cells. Inhibition of HIV-1 production by PAP was also associated with a reduction in intracellular HIV-1 protein levels. Zarling et al., cited supra. This mechanism requires that PAP be present prior to or during viral infection. In CD4+ T cells treated with 5 pM or 50 pM anti-CD4-PAP, we detected approximately 50% or 90%, respectively, lower levels of intracellular gp160 env and $p^{5}5$ and p24 gag proteins 48 hrs after infection when viral proteins were first detected in non-treated infected cells. The finding that PAP inhibits HIV-1 protein expression agrees with other reports that PAP inhibits synthesis of proteins encoded by herpes simplex virus and poliovirus. Ussery et al., *Ann. N.Y. Acad. Sci,* 284, 431 (1977). Although PAP can inactivate the 60S subunit of ribosomes and prevent peptide elongation in vitro, it has also been found that inhibition of HIV-1 antigen production occurred at concentrations of PAP and anti-CD4-PAP well below those which inhibited proliferation of normal CD4+ cells. These observations would suggest that the antiviral action of PAP is due to some activity other than the ribosome specific N-glycosidase activity.

Recently, the cDNA for PAP was cloned and utilized to show that expression of PAP in transgenic plants leads to broad spectrum virus resistance. Lodge et al., *Proc. Natl. Acad. Sci. USA,* 90, 1089 (1993). Furthermore, using yeast as a model system, selection of PAP mutants that are nontoxic to yeast cells is possible. The isolation of PAP mutants that are nontoxic to yeast and have potent antiviral activity against TMV indicate that the ribosome inhibitory activity of PAP can be dissociated from its antiviral activity.

d. Anti-Leukemic Activity of Pokeweed Antiviral Protein

Pokeweed antiviral protein (PAP) has been used as the ribosomal-inhibitory (cytotoxic) moiety of an anti-CD 19 immunotoxin in Phase I/II clinical trials of adult and pediatric patients with acute lymphoblastic leukemia under an Investigational New Drug Application (BB-IND-3864) approved by the Food and Drug Administration. Uckun F M, *Brit. J. Haematol.,* 85, 435 (1993). Anti-CD19 PAP has been developed as an anti-leukemia agent since 1984 and generated very promising results in preclinical leukemia models, which provided the basis for our ongoing clinical investigations. Uckun et al., *Leukemia,* 7, 341 (1993); Uckun et al., *Journal of Experimental Medicine,* 163, 347 (1986).

In a recently completed Phase I/II study, 18 patients with leukemia received escalating doses of anti-CD19 PAP at dose levels ranging from 0.1 μg/kg/day to 250 μg/kg/day x 5 days and 10 patients received anti-CD19-PAP at a fixed dose level of 100 μg/kg/day ×5 days. Uckun FM, Brit. J. Haematol., 85, 435 (1993). A maximum tolerated dose was not reached at the highest dose level of 250 μg/kg/day ×5 days. Patients were given 1 hour i.v. infusions of anti-CD19-PAP on each of five days during one to three courses of treatment. Toxicities included capillary leak syndrome and myalgias. Importantly, no significant hepatic, renal, cardiac, or neurologic toxicity has been observed, and patients have not developed an immune response to either the PAP or monoclonal antibody moiety of anti-CD19 PAP. Thus, the clinical toxicity profile of PAP administered as an immunoconjugate is very different from the reported toxicity profiles of other RIPs. Of the 24 evaluable patients, 5 achieved a complete remission, 2 achieved a partial remission, 5 had partial responses but did not achieve remission, 9 had stable disease and only 3 progressed while on therapy. 4 patients received treatment for minimal leukemia burden: therefore they are not evaluable for objective response. Thus, anti-CD 19-PAP was able to penetrate bone marrow, liver, spleen, and lymph nodes leading to selective eradication of CD19-positive leukemia cells.

E . Production and Purification of Biotherapeutic Agents

1. Immunoconjugates/Immunotoxins a. B43-PAP

Preferred B43-PAP immunotoxins for use in the method are formed by linking an effective cytotoxic amount of PAP molecules to each molecule of B43. For example, a reagent useful in the practice of the invention is an about 1:1 mixture of B43-PAP having one and two PAP molecules per B43 molecule, respectively.

The particular B43-PAP employed in Example 8 (subsections 5–11) hereinbelow is prepared by linking B43 MoAb to wild-type PAP as described in U.S. Pat. No. 4,831,117, to Uckun, which is incorporated herein by reference. A hybridoma secreting B43 is available from the ATCC under designation HB 8903. Further information concerning the production and purification of B43-PAP can be found in Example 8, subsections 1–4. However, B43 can be linked to effective amounts of PAP by other means disclosed in the art, including those taught in U.S. Pat. Nos. 4,363,758, Masuho et al.; 5,167,956, Neville, Jr. et al. and 4,340,535, Voisin et al. For example, in addition to N-succinimidyl 3-(2-pyridyldithio)propionate (SPDP), 4-succinimidyloxycarbonyl-methyl-(2-pyridyldithio)-toluene (SMPT) and N-succimidyl 6-[3-(2-pyridyldithio) propionamido]hexanoate (LC-SPDP) may be used as linking agents. Methods of preparing B43-PAP immunotoxin utilizing these linking agents are also given in Example 8, subsections 2b and 2c.

b. TP3-PAP

Preferred TP3-PAP immunotoxins are formed by linking an effective cytotoxic amount of PAP molecules to each molecule of TP-1 or TP-3. For example, a reagent useful in the practice of the invention is a mixture of TP-3-PAP having 1–3 PAP molecules per TP-3 molecule.

Heterobifunctional cross-linking reagents useful in the formation of monoclonal antibody-PAP immunotoxins include SPDP (N-succinimidyl 3-(2-pyridyldithio) propionate) and its derivatives. For example, the particular TP-3-PAP employed in the examples hereinbelow is prepared by modifying TP-3 MoAb with the crosslinking agent SPDP and then reacting the modified TP-3 with a 3.5:1 molar excess of 2-iminothilane modified PAP.

2. Fusion proteins

DNA encoding recombinant PAP can be derived or isolated from a suitable source, such as a plant source, subsequently chemically altered in vitro, and later introduced into target host cells, such as cells derived from animal, plant, insect, yeast, fungal or bacterial sources. An example of recombinant PAP DNA "derived" from a source, would be a DNA sequence that is identified as a useful fragment encoding PAP, or a fragment, mutant or variant thereof, and which is then chemically synthesized in essentially pure form. An example of such PAP DNA "isolated" from a source would be a useful DNA sequence that is excised or removed from plant cells by chemical means, e.g, by the use of restriction endonucleases, so that it can be further manipulated, e.g., amplified, for use in the invention, by the methodology of genetic engineering.

Therefore, DNA encoding recombinant PAP includes completely synthetic DNA sequences, semi-synthetic DNA sequences, native DNA sequences isolated from plant cells, and DNA sequences derived from introduced RNA, as well as mixtures thereof. Generally, the recombinant DNA sequence is not originally resident in the genome of the host target cell which is the recipient of the DNA, nor is it resident in the genome and not expressed.

The vector comprising recombinant PAP DNA sequence, used for transformation herein, may be circular or linear, double-stranded or single-stranded. Generally, the DNA sequence is in the form of chimeric DNA, such as plasmid DNA, that can also contain coding regions flanked by control sequences which promote the expression of the recombinant DNA present in the resultant transformed host cells. For example, the recombinant DNA may itself comprise a foreign promoter that is active in cells, or may utilize a promoter already present in the genome that is the transformation target. Such promoters include the GAL1 promoter, the T7 promoter, the Lac UV5 promoter, the CMV promoter, as well as the SV 40 late promoter and retroviral LTRs (long terminal repeat elements). Aside from recombinant DNA sequences that serve as transcription units for PAP or portions thereof, a portion of the recombinant DNA may be untranscribed, serving a regulatory or a structural function.

"Control sequences" is defined herein to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a PAP polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The recombinant transformation vector will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as ura, neo, hpt, dhfr, bar, aroA, dapA and the like.

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli,* the beta-glucuronidase gene (gus) of the uidA locus of *E. coli,* and the luciferase gene from firefly *Photinus pyralis.* Expression of the reporter gene is assayed at a suitable time after the DNA has been introduced into the recipient cells.

Other elements functional in the host cells, such as introns, enhancers, polyadenylation sequences and the like, may also be a part of the recombinant PAP. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The general methods for constructing recombinant DNA which can transform target cells are well known to those skilled in the art, and the same compositions and methods of construction may be utilized to produce the recombinant PAP useful herein. For example, J. Sambrook et al., *Molecular Cloning: A Laboratory Manual,* Cold Spring Harbor Laboratory Press (2d ed., 1989), provides suitable methods of construction.

The recombinant PAP can be readily introduced into the target cells by transfection with an expression vector comprising cDNA encoding PAP, for example, by the modified calcium phosphate precipitation procedure of C. Chen et al., *Mol. Cell. Biol.,* 7, 2745 (1987). Transfection can also be accomplished by lipofectin, using commercially available kits, e.g., provided by BRL.

Suitable host cells for the expression of the recombinant PAP are derived from multicellular organisms, such as yeasts, insects and plants. Such host cells are capable of complex processing and glycosylation activities. In principle, any higher eukaryotic cell culture is functional, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technolog,* 6, 47 (1988); Miller et al., in *Genetic Engineering,* J. K. Setlow et al., eds., Vol. 8 (Plenum Publishing, 1986), pp. 277–279; and Maeda et al., *Nature,* 315, 592 (1985). A variety of viral strains for transfection are publicly available, e.g., the L-1 variant of *Autographa californica* NPV and the Bm-5 strain of *Bombyx mori* NPV, and such viruses may be used, preferably for transfection of *Spodoptera frugiperda* cells.

The baculovirus-insect cell system is often used because it closely mimics mammalian expression of proteins, in that proteins can be produced with appropriate post-translational modifications (A. Angermann et al, *Eur. J. Biochem.,* 206, 225 (1992); M. D. Summers et al., *A Manual of Methods for baculovirus Vectors and Insect Cell Culture Procedures of MicroGene System Inc.,* New Haven, Conn. (1988); D. R. O'Reilly et al., *Baculovirus Expression Vectors: Laboratory Manual,* Oxford Univ. Press, N.Y. (1994)).

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. For example, see Lawn et al., *Nucleic Acids Res.,* 9, 6103 (1981), and Goeddel et al., *Nucleic Acids Res.,* 8, 4057 (1980).

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as 32-P, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected piece of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Ouant. Biol.,* 51, 263 (1987); Erlich, ed., *PCR Technology,* (Stockton Press, N.Y., 1989).

"Stringent conditions" are those that (1) employ low ionic strength and high temperature for washing, for example, 0.015M NaCl/0.0015M sodium citrate (SSC); 0.1% sodium lauryl sulfate (SDS) at 50° C., or (2) employ during hybridization a denaturing agent such as formamide, for example, 50% (vol/vol) formamide with 0.1% bovine serum albumin/ 0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5× SSC (0.75M NaCl, 0.075M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS.

When recombinant PAP is expressed in a recombinant cell other than one of human origin, the PAP polypeptide is completely free of proteins or polypeptides of human origin. However, it is necessary to purify PAP polypeptide from recombinant cell proteins or polypeptides to obtain preparations that are substantially homogeneous as to native PAP. For example, the culture medium or lysate can be centrifuged to remove particulate cell debris. The membrane and soluble protein fractions are then separated. The PAP polypeptide may then be purified from the soluble protein fraction and, if necessary, from the membrane fraction of the culture lysate. PAP polypeptide can then be purified from contaminant soluble proteins and polypeptides by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; or ligand affinity chromatography.

Once isolated from the resulting transgenic host cells, derivatives and variants of the PAP polypeptide can be readily prepared. One or more of the residues of the PAP polypeptide can be altered, so long as the antiviral activity is retained. Conservative amino acid substitutions are preferred—that is, for example, aspartic-glutamic as acidic amino acids; lysinelarginine/histidine as basic amino acids; leucine/isoleucine, methionine/valine as hydrophobic amino acids; serine/glycine/alanine/threonine as hydrophilic amino acids. Additionally, salts of carboxyl groups of the polypeptide may be prepared in the usual manner by contacting the polypeptide with one or more equivalents of a desired base, such as, for example, a metallic hydroxide base, e.g., sodium hydroxide; a metal carbonate or bicarbonate base, such as, for example, sodium carbonate or sodium bicarbonate; or an amine base such as, for example, triethylamine, triethanolamine, and the like.

Furthermore acid addition salts of the polypeptides may be prepared by contacting the polypeptide with one or more equivalents of the desired inorganic or organic acid, such as for example, hydrochloric acid.

Esters of carboxyl groups of the polypeptides may be prepared by any of the usual means known in the art for converting a carboxylic acid or precursor to an ester. One preferred method for preparing esters of the present polypeptides, is to cleave the completed polypeptide from the resin in the presence of the desired alcohol either under basic or acidic conditions, depending upon the resin. Thus, the C-terminal end of the polypeptide, when freed from the resin, is directly esterified without isolation of the free acid.

Amides of the isolated polypeptides may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

N-acyl derivatives of an amino group of the present polypeptides may be prepared by utilizing an N-acyl protected or unprotected peptide. 0-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

The following references describe preparation of polypeptide analogs which include non-peptidyl bonds to link amino acid residues. Spatola, *Vega Data,* 1, 3 (1983); Hudson et al., *Int J. Pept. Prot. Res.,* 14, 177 (1979); Spatola in "Chemistry and Biochemistry of Amino Acids, Peptides and Proteins", B. Weinstein, eds., Marcel Dekker, N.Y., p. 267 (1983); Spatola et al., *Life Sci.,* 38 1243 (1986); Almquist et al., *J. Med. Chem.,* 23, 1392 (1980); Holladay et al., *Tetrahedron Letters,* 24, 4401 (1983).

To prepare the fusion protein of the present invention, the PAP gene can be linked either to the gene that encodes the mature form of a cytokine suitable for use in the present invention or a novel genetically engineered monoclonal antibody subunit, e.g., the Fv fragment, preferably at the site of the flexible molecular hinge. In addition, a synthetic DNA sequence encoding a short Ser-(Gly)4-Ser-Met intervening linker can be inserted at the hinge site separating the PAP and cytokine or MoAb scFv moieties to insure that the binding domains would be available for participation in high affinity receptor binding. This rational drug design of recombinant polypeptide cytotoxins is intended to preserve essential structure-function relationships identified in crystallographic analyses of both the PAP and cytokine or antibody molecules. Rambaldi et al., *Blood,* 81, 1376 (1993).

The pET11d expression vector (Novagen, Inc.; 597 Science Drive, Madison, Wis. 53711) employed for the production of recombinant polypeptide cytotoxins in *E. coli* contains a hybrid bacteriophage T7 promoter with a 3'lac operator sequence fusion and an internal copy of lad to suppress basal expression, an efficient Shine-Dalgarno sequence for translational efficiency, and an NcoI cloning site for the insertion of recombinant scFv, dsFv, and toxin gene fusions. The gene encoding the bacteriophage T7 polymerase gene is incorporated by lysogeny into the genome of an *E. coli* expression host and is under the control of the lac UV5 promoter. For example, the pLysS gene in the HMS 174(de3)plysS host produces a low amount of the T7 lysozyme, a natural inhibitor of T7 RNA polymerase, to provide additional stringency of gene expression regulation. Expression of the biotherapeutic agents from within pET11d expression vectors can be induced by the addition of isopropylthiogalactoside (IPTG) to the media containing the *E. coli* expression host.

The biotherapeutic agents are individually expressed in a host such as HMS174(de3)plysS and the soluble product is recovered from cells disrupted by freeze-thaw cycles and sonication. The soluble fraction containing the recombinant polypeptide cytotoxin is subsequently purified through sequential filtration, anti-toxin immunoaffmity chromatography, filtration and dialysis, anion exchange high performance liquid chromatography, additional filtration endotoxin removal resins, and final filtration and dialysis. Insoluble product can be rendered to a soluble form for purification by dissolution in 7M guanidine HCl with a slow renaturation under controlled conditions to a physiological buffer such as phosphate buffered saline.

F. Modes of Administration of the Biotherapeutic Agents

The present biotherapeutic agents or free recombinant PAP and variants, subunits or mutants thereof can be formulated as pharmaceutical compositions and administered to a human or other mammal afflicted with a condition treatable by these agents, alone or in combination in a unit dosage form comprising an effective amount of one or more of these agents in combination with a pharmaceutically acceptable carrier or vehicle.

1. Dosage Forms

It is preferred that the biotherapeutic agents or free recombinant PAP of the present invention be parenterally administered, i.e., intravenously, or subcutaneously by infusion or injection. Solutions or suspensions of the biotherapeutic agents or free recombinant PAP can be prepared in water, or isotonic saline, such as PBS, optionally mixed with a nontoxic surfactant. Dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms. Additionally, more specific delivery of the biotherapeutic agents or free recombinant PAP to the lungs may be accomplished via aerosol delivery systems. The pharmaceutical dosage form suitable for aerosol delivery can include adipot formulations such as a liposome of suitable size.

The pharmaceutical dosage form suitable for injection or infusion use can include sterile aqueous solutions or dispersions or sterile powders comprising the biotherapeutic agents which are adapted for the extemporaneous preparation of sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the biotherapeutic agents or free recombinant PAP in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile- filtered solutions.

Furthermore, suitable formulations for the biotherapeutic agents or free recombinant PAP of the present invention include those suitable for oral, rectal, nasal, topical (including, ocular, and sublingual) or vaginal administration or in a form suitable for administration by inhalation or insufflation. The formulations may be prepared by any of the methods well known in the art of pharmacy. Such methods include the step of bringing into association the biotherapeutic agent with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The biotherapeutic agents and free recombinant PAP may also be formulated for intra-nasal or ocular adininistration. In this form of administration, the active ingredient may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays are conveniently delivered from pressurized packs.

For administration by inhalation, the biotherapeutic agents or free recombinant PAP are conveniently delivered from an insufflator, nebulizer or a pressurized pack or other convenient means of delivering an aerosol spray. Pressurized packs may comprise a suitable propellant such as dichlorodifluoromethane, trichlorofluromethane, dichlorotetrafluoroethane, carbon dioxide or other suitable gas. In the case of a pressurized aerosol, the dosage unit may be determined by providing a valve to deliver a metered amount.

Alternatively, for administration by inhalation of insufflation, the biotherapeutic agents or free recombinant PAP may take the form of a dry powder composition, for example, a powder mix of the compound or a suitable powder base such as lactose or starch. The powder composition may be presented in unit dosage form in, for example, capsules or cartridge or e.g., gelatin or blister packs from which the powder may be administered with the aid of an inhaler of insufflator.

Additionally, the biotherapeutic agents as well as the free recombinant PAP are well suited to formulation or controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdernal delivery, subcutaneous implants, infusion pumps or via release from implanted depot sustained release dosage forms.

2. Dosages

The dosage of the biotherapeutic agents in said composition can be varied widely, in accord with the size, age and condition of the patient and the target cancer. Based on animal data, it is expected that the dosage can be varied between 0.025 mg/kg/day and I mg/kg/day, administered over a period of about 3 to 5 days.

The invention will be further described by reference to the following detailed examples.

EXAMPLE 1

Construction of Yeast Expression Vectors and Analysis of PAP Expression in Yeast The full length cDNAs corresponding to PAP and PAP-v (variant PAP) disclosed in Lodge et al., and shown in Table 1, were cloned into yeast expression vectors, under the control of the galactose inducible promoter, GAL1. *S. cerevisiae* was chosen as the expression system because yeast has the advantage of supplying the eukaryotic cell-specific post-translational modifications. Since yeast ribosomes are sensitive to PAP, a regulated promoter was used to drive the expression of PAP. The cDNAs encoding PAP and PAP-v were cloned into the yeast expression vector pAC55, containing the selectable marker URA3, as Bgl II/Smal fragments under the control of the galactose inducible promoter pGa11. The vectors containing PAP (NT123) and PAP-v (NT124) were transformed into the yeast strain W303 (Mat a, ade2-1 trpl-1 ura3-1 leu2-3, 112 his3-1 1, 15can1–100 (Bossie et al., *Mol. Biol. Cell,* 3, 875 (1992)) according to the procedure described in Ito et al., *J. Bacteriol.,* 153, 163 (1983), and transformants were selected on uracil minus media with glucose at 30° C.

Yeast cells containing either NT123 (wild-type PAP) or NT124 (PAP-v) were grown in uracil minus medium with 2% raffinose at 30° C. for 48 hours to a density of $5\times10^7$ cells/ml. PAP protein expression was induced by the addition of 2% galactose to half of the culture, while the other half of the culture was used as an uninduced control. The cells were allowed to grow for an additional 4 hours and then collected by centrifugation at 10,000 g for 5 minutes. The cells were resuspended in RIPA buffer (9150 ml NaCl, 1% NP-40, 0.5% sodium deoxycholate, 0.1% SDS, 50 mM Tris-HCl, pH 8.0) with protease inhibitors (0.1 μg/ml each of antipain, aprotinin, chymostatin, leupeptin, pepstatin) and lysed using glass beads (0.5 mm). Extracts were loaded on a 10% SDS-PAGE gel. Immunoblot analysis was performed by the enhanced chemiluminescence (ECL) method (Amersham), using antibodies against purified PAP.

Both PAP and PAP-v were expressed in yeast after galactose induction. Based on comparison with PAP protein standards, yeast cells containing the PAP plasmid (NT123) expressed both the mature form of PAP and a larger form, while cells containing the PAP-v (NT124) expressed predominantly the larger form and very low levels of the mature form. PAP was not detected in the culture medium. These results suggest that (1) PAP is expressed as a precursor and processed to the mature form in yeast; and (2) PAP undergoes further processing in addition to the co-translational cleavage of the amino acid N-terminal signal peptide described by Lodge et al., cited supra, because the size of the mature PAP and the PAP expressed in yeast was found to be smaller than the expected size after the removal of the signal sequence.

EXAMPLE 2

In Vitro Translation and Processing of PAP and PAP-v

To examine the processing of PAP in vitro, both constructs described in Example 1 were transcribed and translated in vitro using the T7 coupled reticulocyte lysate translation system in the presence of $^{35}$S-methionine with or without canine microsomal membranes (Promega). PAP and PAP-v cDNAs were cloned into the pGem 3Z vector (Promega) downstream of the T7 promoter. An equal amount of DNA (1 μg) from each construct was transcribed and translated in vitro in the presence of $^{35}$S methionine, using the T7 coupled reticulocyte lysate translation system (Promega) with or without canine pancreatic microsomal membranes (Promega). Translation products were incubated with 0.2 mg/ml proteinase K in the presence of 5 mM EDTA and 125 mM sucrose for 90 minutes. Proteinase K was inactivated by addition of 4 mM PMSF and incubation at room temperature for 2 hours. Translation products were then treated with Endo-H (endo-N-acetylglucosaminidase (1 mU/10 μl) in the presence of 0.1% SDS and 0.1M sodium citrate pH 5.5, at 37° C. for 12 hours. Equal amounts of protein (3.5 μl) were analyzed on 10% SDS-PAGE in accordance with the procedure described in Laenunlie et al., *Nature,* 277, 680 (1970).

PAP and PAP-v encode precursor proteins of 33 and 34 kDa, respectively, and both precursors are processed to a 32 kDa form after incubation with membranes. The processed proteins are still larger than the mature form (29 kDa), indicating that the PAP precursor undergoes further post-translation processing. PAP does not contain any N-linked glycosylation sites and the size of the in vitro translated proteins did not change after treatment with Endo H, which removes carbohydrate. These results indicate that the PAP precursors contain an N-terminal signal sequence which is co-translationally removed. Further evidence for C-terminal processing was obtained from X-ray structure analysis, which showed that mature PAP is 29 amino acids shorter at its C-terminus than the sequence predicted from cDNA. See Monzingo et al., *J. Biol.* 233, 705 (1993).

EXAMPLE 3

Growth of Transformed Yeast

In the presence of 2% raffinose, a non-repressing, non-inducing carbon source relative to GAL gene expression, the growth of yeast transformants containing NT123 or NT124 was indistinguishable from the transformants containing the vector alone. Growth of transformed yeast containing NT123 was arrested upon addition of the inducer, galactose, to the medium. Cells containing NT123 or NT124 did not grow on plates containing galactose. In the liquid medium, however, the extent of inhibition was greater with NT123 than NT124, possibly due to lower levels of mature PAP produced in yeast containing NT124. PAP expression was detected within 2 hours of galactose addition to the medium. Maximal levels were reached in 6 to 8 hours. Immunoblot analysis using antibodies against PAP detected a maximum PAP level of 1 μg/mg yeast protein in NT123 transformants and 250 ng/mg yeast protein in NT124 transformants. These results were consistent with production of active PAP in yeast.

EXAMPLE 4

Mutagenesis of PAP plasmids

To isolate PAP mutants nontoxic to yeast, the expression plasmids containing PAP (NT123) or PAP-v (NT124) were mutagenized using hydroxylamine, transformed into yeast and cells were plated on medium containing glucose and replica plated onto galactose containing plates. About 10 μg of the purified plasmid DNA were added to 50 μl of freshly prepared hydroxylamine solution (0.35 g hydroxylamine-HCl and 0.09 g NaOH in 5 mL of water) and incubated at 37° C. for 20 hours. To stop mutagenesis, 10 μl of 5M NaCl, 50 μl of 1 mg/ml BSA and 1 ml of 100% ethanol were added and the mutagenized DNA was replicated by incubation at −70° C. for 10 minutes. The DNA was resuspended in TE and precipitated again. The DNA was then transformed into yeast and plated on uracil minus medium containing 2% glucose and replica plated on medium containing 2% galactose. The colonies that grew on galactose were analyzed for PAP expression by ELISA as described by Lodge et al., cited supra, and by immunoblot analysis to identify the mutants which expressed hydroxylamine generated mutant PAP.

EXAMPLE 5

Growth of Mutant Yeast

Growth of mutants derived from NT123 on galactose containing medium was indistinguishable from growth on raffinose containing medium. Similar results were obtained with mutants derived from NT124. Analysis of protein accumulation in yeast indicated that the expression of wild-type PAP, but not the hydroxylamine generated mutant PAP, resulted in decreased protein accumulation in yeast.

After mutagenesis, the colonies growing on uracil deficient galactose plates were analyzed for PAP expression by ELISA using anti-PAP antibodies and the positives were further analyzed by immunoblot analysis. Of a total of 28 mutants from NT123 mutagenesis, six different isolates expressed proteins which cross-reacted with PAP antibodies. Out of 44 mutants isolated from NT124 mutagenesis, 24 different isolates produced proteins which cross-reacted with PAP antibodies. Four mutants (HMNT123-1, 124-6, 124-7 and 124-1) produced proteins which were larger than the mature form of PAP (29 kDa), suggesting that the processing of PAP to the mature form is blocked in these mutants. Two mutants (HMNT123-2 and 123-3) produced proteins that co-migrated with the mature form of PAP, while several others (HMNT123-4, 123-5, 123-6, 124-2 and 124-3), produced smaller proteins. The protein expression levels in the mutants ranged from 0.005 to 0.08% of total soluble protein.

EXAMPLE 6

Nucleotide Sequence Analysis of PAP mutants

The positions of the amino acid alterations in the PAP mutants were identified by sequence analysis of the plasmids rescued from yeast. Plasmids were isolated from the mutants, transformed into *E. coli* according to the procedure described by Rose et al., cited supra, and sequenced using the Sequenase 2.0 DNA sequencing kit (USB). See Robzyk et al., *Nucl. Acid Res.,* 20, 3790(1992). Sequence analysis of HMNT123-2 revealed that it contains a single point mutation, changing the glutamic acid at position 176 to valine (E176V) at the putative active site (Table 2). HMNT123-2 produced a protein of the same size as the wild-type PAP.

Glutamic acid at position 176 (E176) is highly conserved among all RIPs sequenced to date and it is proposed to be at the active site cleft of PAP. HMNT123-6, HMNT124-2 and HMNT124-3 all had a point mutation near the C-terminus which introduced a stop codon instead of a tryptophan at position 237 (W237) (Table 2). As a result of this mutation, 26 amino acids were deleted from the C-terminus of the mutant PAP, and a truncated protein was produced. HMNT123-5 contained a frameshift mutation, which deleted two nucleotides (GA) at about the codon for Glu184 (GAG), whereby the reading from was altered and the Asn190 codon became TAA because the reading frame shifted to the −1 position. A point mutation in 1 24-1 (SEQ ID NO:6) changed the glutamic acid at position 97 to lysine (E97K) (Table 2). HMNT123-1 (SEQ ID NO:2) also contained a single point mutation, at position 75, changing glycine to valine (G75V). Both of these mutants expressed a larger protein that purified mature PAP, suggesting that processing of PAP is inhibited in these mutants.

To confirm that the observed mutant phenotypes were due to the mutations identified in the PAP sequence, and not due to a chromosomal mutation, each mutant PAP plasmid was isolated and re-transformed into the host strain, W303, and URA+ transformants were selected. These transformants grew at wild type rates on galactose containing medium, indicating that the ability of the transformants to survive induction of PAP expression is plasmid-linked.

TABLE 2

Mutations which Abolish the Cytotoxicity of PAP to Eukaryotic Cells

| | |
|---|---|
| HMNT123-1 | Gly-75 (GGT) → Val (GTT) |
| HMNT123-2 | Glu-176 (GAG) → Val (GTG) |
| HMNT123-4 | Trp-208 (TGG) → Stop (TAG) |
| HMNT123-5 | Glu-184 (GAG) → Glu (GAA) |
| HMNT123-6 | Trp-237 (TGG) → Stop (TAG) |
| HMNT124-1 | Glu-97 (GAA) → Lys (AAA) |
| HMNT124-2 | Trp-237 (TGG) → Stop (TAG) |
| HMNT124-3 | Trp-237 (TGG) → Stop (TAG) |
| HMNT124-13 | Leu-202 (CTT) Phe (TTT) |

EXAMPLE 7

Enzymatic Activity of PAP Mutants

An in vitro translation assay was used to compare the enzymatic activity of PAP mutants. Brome mosaic virus (BMV) RNA was translated in the rabbit reticulocyte lysate system (Promega) in the presence of extracts from yeast containing different amounts of PAP, as described in Lodge et al., cited supra. PAP levels in yeast were quantitated by ELISA (Lodge et al., cited supra). The inhibition curves were linear in the range of 0.1 to 1 ng PAP/mL. Table 3 shows the results of the protein synthesis inhibition assay carried out in the presence of 0.2 ng/ml PAP from yeast. The amount of total protein and PAP were adjusted to 87 ng/ml and 0.2 ng/ml, respectively, in each extract by adding either wild-type yeast extract or RIPA buffer. In previous experiments, when in vitro translation was performed in the presence of 0.2 ng/ml BSA, no inhibition of translation was observed. When 0.2 ng/ml protein from nontransformed yeast (WT) were added, a slight inhibition of translation was observed. Translation was inhibited in the presence of 0.2 ng/mi of: (1) purified PAP added to wild-type yeast extract (WT+PAP); (2) protein extracts from yeast containing NT123 or NT124; and (3) protein extracts from yeast containing the hydroxylamine generated mutants HMNT123-3, HMNT124-1 (SEQ ID NO:6), HMNT24-3 (SEQ ID NO: 14) and HMNT124-13 (SEQ ID NO:15). In contrast, protein extracted from HT123-2 (SEQ ID NO:9) did not inhibit protein synthesis in the reticulocyte lysate system. Similar results were obtained when in vitro translation experiments were performed using 0.1 ng/ml PAP.

TABLE 3

Inhibition of Protein Synthesis by PAP Mutants.

| Protein added to translation medium | Protein synthesis[1] |
|---|---|
| No RNA | 2,246 ± 204 |
| BSA | 244,956 |
| WT | 176,723 ± 713 |
| PAP + WT | 146,660 ± 2474 |
| NT123 | 110,007 ± 445 |
| HMNT123-2 | 213,952 ± 767 |
| HMNT123-3 | 134,202 ± 5522 |
| HMNT124 | 84,959 ± 661 |
| HMNT124-1 | 119,529 ± 2094 |
| HMNT124-3 | 132,955 ± 3739 |
| HMNT124-13 | 145,899 ± 4457 |

[1]cpm incorporated

EXAMPLE 8

Studies conducted with B43-PAP (wild-type) immunotoxin

Highly purified preparations of B43 MoAb and wild-type PAP were used as the starting materials for the scaled-up preparation of B43-PAP immunotoxin. All column eluants were tested for sterility and the presence of endotoxin (using the Limulus amebocyte assay) prior to use. All of the following steps in the preparation and purification of B43-PAP immunotoxin were performed under GLP conditions using sterile, endotoxin-free buffers and equipment. Additionally, the following protocol illustrates the preparation of a B43-PAP utilizing wild-type PAP. The same protocol could be utilized to produce a B43-PAP immunotoxin with variant PAP (PAP-υ).

1. Modification of B43 MoAb and PAP

In brief, purified B43 MoAb, at a concentration of 10 mg/ml in 40 MM sodium phosphate, 150 mM sodium chloride, pH 7.5 (PBS) was reacted with a 3:1 molar excess of SPDP (N-succinimidyl 3-(2-pyridyldithio) propionate (Pharmacia LKB, Piscataway, N.J.), freshly prepared in DMSO (HybriMax grade, Sigma Chemical Co., St. Louis, Mo.), at a concentration of 64 mM, and diluted 1/10 in PBS just prior to use. Purified PAP, at a concentration of 10 mg/ml in PBS pH 8, was mixed with a three-fold molar excess of 2-iminothiolane HCl (Pierce Chemical Co., Rockford, Ill.), prepared immediately prior to use as a 20 mM solution in 50 mM sodium phosphate, pH 8.6. Both modification reactions were allowed to proceed for 2 hours at room temperature with gentle rocking in sterile, endotoxin-free vials (Miles, West Haven, Conn.). Excess reagents and low molecular weight reaction products were subsequently removed by gel filtration on Sephadex G-25 PD-10 prepacked columns (Pharmacia LKB) equilibrated in sterile, endotoxin free PBS, pH 7.5. Individual fractions were monitored at 280 nm and those containing the majority of the protein were combined and the total amounts of antibody and PAP calculated using $E^{1\%}_{280nm}$ values of 1.40 and 0.83 for B43 and PAP respectively.

The extent of amino group modification of B43 MoAb was determined by measuring the liberation of pyridine-2-thione groups following treatment with dithiothreitol (DTT). The concentration of the liberated groups was calculated by using the extinction coefficient $E_{343nm}=8.08\times10^3\ M^{-1}$. Thiolation of PAP by 2-iminothiolane was determined following treatment with Ellman's reagent (DTNB). The absorbance at 412 nm was measured and the number of sulfhydryl groups introduced per mole of PAP was calculated using an extinction coefficient of $13.6\times10^3\ M^{-1}$.

2. Conjugation of B43 MoAb and PAP.

a. Utilizing SPDP as a linking agent.

2-iminothiolane-derivatized PAP was added to the SPDP-modified B43 MoAb at a final molar ratio of 3.5:1, PAP:MoAB. This mixture was incubated for 2 hours in sterile, endotoxin free vials at room temperature with gentle rocking and left at 4° C. overnight. Gentle rocking was continued for 4–5 hours the following day before the reaction mixture was filtered (0.2 μm Acrodisc, Gelman Sciences, Ann Arbor, Mich.) in preparation for the HPLC step.

b. Utilizing LC-SPDP as a linking agent

Initially, the procedure of part I was followed, with the substitution of LC-SPDP for SPDP to introduce 2-pyridyl disulfide bonds into B43 MoAb. A 47 mM solution of LC-SPDP in DMSO was freshly prepared and diluted 1:10 in PBS immediately prior to use. Modified PAP was added to the LC-SPDP-modified B43-MoAb at a final molar ration of 3.5:1, PAP:MoAb. This mixture was incubated for 2 hours in sterile, endotoxin free vials at room temperature with gentle rocking and left at 4° C. overnight. Gentle rocking was continued for 4–5 hours the following day before the reaction mixture was filtered (0.2 μm Acrodisc, Gelman Sciences, Ann Arbor, Mich.) in preparation for the HPLC step.

c. Utilizing SMPT as a linking agent

For modification with SMPT, the published procedure of Thorpe was used. *Cancer Res.,* 47, 5924 (1987). Step 1 was replaced with the following procedure. Briefly, 20 mg of B43 were dialyzed overnight against 50 mM sodium borate buffer, pH 9.0, containing 1.7% (w/v) sodium chloride. and subsequently reacted with a 2.4:1 molar ratio of SMPT. Dimethylformamnide was added to the MoAb at a fmal volume of 10% in order to keep the SMPT soluble. Purified PAP (10 mg/ml in PBS, pH 8.0) was modified via its free amino groups with a 3:1 molar excess of 2-iminothiolane HCl (Pierce Chemical Company) prepared immediately prior to use as a 20 mM solution in 50 mM sodium phosphate buffer, pH 8.6. The modification reaction was carried out in endotoxin-free, glass vials at room temperature for 2 hours with gentle rocking. Excess reagents and low molecular weight reaction products were subsequently removed from the derivatized PAP and B43 MoAb by gel filtration on Sephadex G-25 PD-10 prepacked columns (Pharmacia LKB) equilibrated in "phosphate-EDTA" buffer containing 10 mM $Na_2HPO_4$+1.8 mM $KH_2PO_4$ +170 mM NaCl+3.4 mM KCl+1 mM EDTA, pH 7.5. Individual fractions were monitored at 280 nm and those containing the majority of the protein were combined and the total amounts of PAP and MoAb calculated using E $1\%/_{280nm}$ values of 0.83 and 1.4 for PAP and B43, respectively. Thiolation of PAP by 2-iminothiolane was determined following treatment with Ellman's reagent (DTNB). The absorbance at 412 nm was calculated using an extinction coefficient of 13.6×$10^3$ $M^{-1}$. The extent of amino group modification of B43 MoAb was determined by measuring the release of pyridine-2-thione groups following treatment with dithiothrieitol (DTT). The concentration of these liberated groups was calculated using the extinction coefficient $E_{343nm}$=8.08×$10^3$ $M^{-1}$.

Modified PAP was added to the SMPT-derivatized B43-MoAb at a final molar ration of 2.5:1, PAP:MoAb. This mixture was incubated for 2 hours in sterile, endotoxin free vials at room temperature with gentle rocking and left at 4° C. overnight. Gentle rocking was continued for 72 hours the following day before the reaction mixture was filtered (0.2 $\mu$m Acrodisc, Gelman Sciences, Ann Arbor, Mich.) in preparation for the HPLC step.

3. Purification of B43-PAP immunotoxin.

The reaction mixture of Example 3, part 2a was subjected to gel filtration chromatography by HPLC to remove unreacted PAP as well as high molecular weight (>300 kDa) conjugates/aggregates. A 21.5×600 mm Spherogel TSK-3000-SW column (TosoHaas and Beckman Instruments) was used and was equilibrated in 100 mM sodium phosphate buffer, pH 6.8, at a flow rate of 3 ml/min.

Ion-exchange chromatography on CM-Sepharose (Pharmacia LKB, Piscataway, N.J.) was used to further purify B43-PAP immunotoxin from unconjugated B43 MoAb. 200 mg batches of the semipurified B43-PAP immunotoxin from the HPLC step were concentrated to 10 mg/ml using the Centriprep 30 devices (Amicon, Danvers, Mass.) and equilibrated by dialysis in 10 mM sodium phosphate buffer, pH 6.2 at 4° C. Spectro/Por 2 tubing was used and the 1500 ml buffer changed twice at 12 hour intervals. The CM-sepharose column (5×12 cm), containing 230 ml of resin was equilibrated in 10 mM sodium phosphate buffer, pH 6.2 and the pH as well as the conductivity of the column effluent were measured. The dialyzed sample (20 ml) was diluted to 100 ml using 10 mM sodium phosphate, pH 6.2, and the pH and conductivity were measured before applying the sample to the column at a flow rate of 1 ml/min. When the sample had completely drained into the resin, the column was washed with the pH 6.2 buffer until the peak of unconjugated antibody came through and the absorbance at 280 nm returned to baseline.

B43-PAP immunotoxin was subsequently eluted from the CM-Sepharose column using 10 mM sodium phosphate buffer, pH 7.8, containing 20 mM sodium chloride. The ascending portion of the immunotoxin peak was collected in 5 ml fractions as the absorbance at 280 nm began to increase. A small peak or early shoulder occasionally eluted immediately prior to the large immunotoxin peak. This material was contaminated with a small amount of antibody (usually<5% of the initial amount of B43 MoAb) and was kept separate. The rest of the large peak, containing the 180 kDa and 210 kDa species (i.e., 1:1 and 2:1 molar ratio of PAP:MoAb) of B43-PAP immunotoxin was collected in two or three fractions and the column washed at pH 7.8, containing 150 mM sodium chloride, was used to elute any remaining immunotoxin. Fractions containing purified 180 kDa and 210 kDa B43-PAP immunotoxin species were combined, brought to 40 mM sodium phosphate, 150 mM sodium chloride, pH 7.5, concentrated to 1.0 mg/ml, filter-sterilized, and frozen at −70° C. until use. Protein concentrations were determined for the B43-PAP conjugates using the Bicinchoninic Acid Protein Assay kit obtained from Sigma Chemical Co. (St. Louis, Mo.). The conjugation of B43 MoAb to PAP was routinely monitored using 5% (non-reduced) SDS-PAGE separating slab gels and the Bio-Rad Mini Protean II apparatus.

4. Endotoxin Removal

The Affi-Prep Polymyxin Support (obtained from Bio-Rad Laboratories, Richmond, Calif.) was used to remove endotoxin from the purified B43-PAP immunotoxin preparations. Talmadge et al., *J. Chromatogr.,* 476, 175 (1989). The resin was washed ten times with sterile, endotoxin-free water (Travenol Laboratories, Deerfield, Ill.), followed by two washes in sterile, endotoxin-free sodium phosphate buffer, pH 7.5, containing 150 mM sodium chloride. 20 ml of B43-PAP, at a concentration of 1.5 mg/ml, were added to 12 ml of washed Affi-Prep Polymyxin resin in a sterile and pyrogen-free 50 ml centrifuge tube. The mixture was gently rotated overnight at 4° C. (20–24 hours), then centrifuged to pellet the resin. The immunotoxin-containing supernatant was carefully removed and sterile-filtered into a sterile, endotoxin-free glass vial. 5 ml of additional sterile PBS were added to wash the resin. Following centrifugation, this supernatant was filtered into the same glass vial and a sample removed for the Limulus amebocyte lysate (LAL) assay.

5. In Vivo Toxicity and Pharmacokinetic Properties of PAP. B43 MoAb. and B43-PAP Immunotoxin All animal studies were performed under GLP conditions and following the U.S. Government Principles for the Utilization and Care of Vertebrate Animals, Used in Testing, Research, and Training and according to the guidelines of the University of Minnesota Animal Care Committee. Female BALB/c mice (6–8 weeks old, 15–17 g) were obtained from NIH and were maintained in the ALAAC accredited facilities of the University of Minnesota Research Animal Resources.

In acute toxicity studies, mice were given i.p. or i.v. injections of 0–250 $\mu$g PAP, 0–10,000 $\mu$g B43 MoAb; or 0–250 $\mu$g purified B43-PAP immunotoxin in 0.2 ml PBS. Deaths were recorded twice daily and $LD_{50}$ values were determined for 10 day survival. Groups of 5–8 mice were used for each of ten different treatment doses, and the experiments were repeated four times.

In pharmacokinetic studies, mice were lightly anesthetized with ether and injected i.v. with 50–250 $\mu$g B43-PAP immunotoxin in 0.5 ml PBS. Mice were serially bled by retroorbital puncture at 10 minutes, 30 minutes, 1 hour, 2 hours, 4 hours, 8 hours, 12 hours, 24 hours and 48 hours following the administration of immunotoxin. The in vivo stability of B43-PAP immunotoxin was examined by solid-phase ELISA determinations using (1) Falcon Micro Test 111 culture plates coated with affinity purified polyclonal rabbit anti-PAP IgG and (2) goat anti-mouse IgG conjugated to peroxidase, as described above, for the detection of B43 MoAb in ECS supernatants.

6. Studies in Mouse Models of CD19± Human B-lineage ALL

A highly aggressive subclone of the human pre-B acute lymphoblastic leukemia cell line NALM-6 causes disseminated and fatal leukemia in CB.17 mice with severe combined immunodeficiency (SCID) even after intravenous injection of a single cell. An intravenous challenge with $1\times10^6$ NALM-6-UM1 cells caused 15 of 27 (56%) SCID mice to become paraplegic at 31±2 days (median=33 days) and 27 of 27 (100%) mice to die of disseminated human pre-B ALL at 38±1 days (median=39 days). Uckun et al., *Blood* 79, 2201 (1992). This SCID mouse model of aggressive human pre-B ALL was used to evaluate the in vivo anti-leukemic efficacy of B43-PAP.

A three-day treatment with non-toxic doses of B43-PAP markedly reduced the incidence of paraplegia and improved event-free survival in SCID mice challenged with $1\times10^6$ NALM-6-UM1 pre-B ALL cells, as reflected by significantly higher cumulative proportions of mice free of paraplegia or alive for one to seven months, as compared to PBS treated control mice. The Kaplan-Meier estimates and standard errors of the probability of developing paraplegia after inoculation of $1\times10^6$ NALM-6-UM1 cells were 64±10% for PBS treated mice (median time to paraplegia=37 days) (N=27), 18±8% for mice treated with 15 $\mu$g B43-PAP (5 $\mu$g/mouse/day×3 days) (N=23) and 5±5% for mice treated with 30 $\mu$g B43-PAP (10 $\mu$g/mouse/day×3 days) (N=21).

While 27 of 27 PBS treated control SCID mice died of leukemia at 38±1 days (range=24 to 54 days), only 16 of 44 B43-PAP treated mice developed leukemia at 74±12 days (range=30 to 182 days), consistent with ≧6 logs kill of clonogenic NALM-6-UM 1 cells in 64% of SCID mice. Uckun et al., *Blood,* 79, 2201 (1992). The Kaplan-Meier estimates and standard errors of the probability of long-term event-free survival after inoculation of $1\times10^6$ NALM-6-UM1 cells were 65±10 % for mice treated with 15 $\mu$g B43-PAP and 60±11% for mice treated with 30 $\mu$g B43-PAP with a median survival time of >7 months for both groups.

Long-term survivors in the B43-PAP treated groups were electively sacrificed at 7 months to assess their leukemia burden. No histopathologic, flow cytometric, or PCR evidence of pre-B ALL was found. The activity of B43-PAP appears similar or superior to that of other conventional cytotoxic agents at clinically attainable and tolerable AUC's.

7. Studies in Cynomologous Monkeys

In non-human primate toxicity studies, a total of 10 cynomologous monkeys were given escalating doses of B43-PAP. No histopathologic lesions were found in monkeys given 7 intravenous doses of B43-PAP at dose levels of 0.001 mg/kg/day (Total dose=0.007 mg/kg), 0.01 mg/kg/day (Total dose=0.07 mg/kg), or 0.05 mg/kg (Total dose=0.35 mg/kg) on alternate days, or in monkeys given 7 intravenous doses of B43-PAP on consecutive days at dose levels of 0.01 mg/kg/day (Total dose=0.07 mg/kg) or 0.1 mg/kg/day (Total dose=0.7 mg/kg). In these monkeys, the only clinical/laboratory signs of toxicity were a mild (<2-fold) and transient elevation of transaminases and a mild capillary leak syndrome (only at doses ≧0.35 mg/kg). However, several lesions were found in monkeys given 7 intravenous doses of B43-PAP on 7 consecutive days at dose levels of 0.5 mg/kg/day (Total dose=3.5 mg/kg) or 1.0 mg/kg/day (Total dose=7.0 mg/kg). These lesions included acute mild multifocal hepatocellular necrosis and hepatitis at the 1.0 mg/kg/day dose level and severe subacute renal tubular necrosis at both dose levels.

The stability (chemical, biological, and immunological) and immunogenicity (induction of host immune responses to PAP as well as murine IgG moieties) of B43-PAP in cynomologous monkeys was also evaluated. The serum half-life of B43-PAP in cynomologous monkeys ranged from 18.2 hrs to 22.6 hrs. The kinetics as well as the magnitude of the humoral immune response of cynomologous monkeys to the PAP or the murine IgG moieties of B43-PAP were dependent on the immunotoxin dose administered.

8. Phase I/II Clinical Studies in Patients with Therapy Refractory and Steroid Resistant ALL Twenty-four patients (4 adults and 20 children) with therapy refractory and steroid resistant ALL have received 1–3 cycles of B43-PAP therapy. These patients had relapsed after multiple courses of intensive chemotherapy and/or total body irradiation plus chemotherapy and had failed attempts to control their disease with a combination of multiple standard chemotherapeutic agents. During each 5-day treatment cycle, B43-PAP was administered daily as a I hour intravenous infusion. Prior to and following each infusion, the catheter line was cleared with normal saline, or dextrose, 5% in ½ normal saline. 50 mg/m$^2$ hydrocortisone was added to each B43-PAP bag to minimize the risk of allergic reactions. The infusion was not interrupted for blood drawing or for administration of other medications. Except for capillary leak and myalgias, no other significant toxicities were observed at dose levels ranging from 0.1 $\mu$g/kg/day to 250 $\mu$g/kg/day. Significant myelosuppression, nephrotoxicity, hepatotoxicity, or cardiac toxicity was not observed. Five patients achieved complete remission, two patients achieved a partial remission, 5 patients (all with M3 marrow status with large numbers of circulating leukemia cells) had partial responses (marked reduction or eradication of circulating leukemia and shrinkage of lymph nodes/spleen without a significant decrease in the percentage of bone marrow blasts), 9 patients had a stable disease while on B43-PAP therapy and only 3 patients had progressive leukemia despite B43-PAP.

B43-PAP was very stable and therapeutic concentrations of >0.1 $\mu$g/ml of serum could be maintained by a single infusion per day for 12–24 hours in all patients receiving B43-PAP at the stage II dose of 100 $\mu$g/kg/day. Concentrations as high as 13 $\mu$g/ml were well-tolerated by patients.

Only 3 of 24 patients developed antibodies to the murine MoAb moiety as well as the PAP moiety of B43-PAP immunotoxin. This result indicates that at therapeutic doses B43-PAP will effectively kill or inhibit functional B-cells and no significant host immune response will be triggered in the majority of patients.

9. In Vitro Anti-HIV Activity of PAP and Immunoconjugates Containing PAP

In initial studies, the effects of purified native PAP on HIV-1 production in primary human CD4+ cells was tested. Uckun et al., *Nature,* 347, 92 (19??). The 50% inhibitory dose ($ID_{50}$) for HIV-1 p24 production, in both primary CD4+ T-cells and macrophages, was $5\times10^3$ pM PAP. PAP was covalently linked to MoAbs reactive with the CD5, CD7 and CD4 antigens, expressed on CD4+ T cells, as previously described by Myers et al. *Journal of Immunological Methods,* 136, 221 (1991). The $ID_{50}$ for HIV-1 p24 production was 50 pM for anti-CD5-PAP, 6 pM for anti-CD7-PAP and 1 pM for anti-CD4-PAP. In contrast, PAP conjugated to anti-CD19, which reacts with B cells but not CD4+ T cells, caused 7 only 20% inhibition of p24 production even at $1\times10^3$ pM. Zarling et al., *Nature,* 347, 92 (1990). Anti-CD4-PAP was found to be approximately 5000 times more potent than non-conjugated PAP at inhibiting HIV-1 replication in primary CD4+ cells. Id. Only at concentrations at least 103 times the $ID_{50}$ for p24 production did anti-CD4-PAP cause 50% inhibition of proliferation of PHA-stimulated uninfected CD4+ T cells or colony formation by bone marrow progenitor cells. Although non-conjugated anti-CD4 can also inhibit HIV-1 replication by binding to the CD4 molecule, the receptor for HIV-1 gp120, it was found that inhibition of HIV-1 production occurred only at G17.2 (anti-CD4) monoclonal antibody concentrations exceeding $7\times10^3$ pM (1 μg/ml). Id.

Several PAP-immunoconjugates were tested for their ability to inhibit HIV-1 production in patients' T-cells that were stimulated with anti-CD3. Anti-CD4-PAP, which is the most specific conjugate for targeting PAP to CD4+ cells, was also found to be the most potent conjugate at inhibiting HIV-1 production. Virtually complete inhibition of HIV-1 production occurred at concentrations as low as 0.5 pM, whereas a concentration 100 times higher did not inhibit proliferation of the stimulated PBL. Notably, treatment of patients' anti-CD3-activated peripheral blood lymphocytes with 5 pM anti-CD4-PAP inhibited production of HIV-1 for at least 22 days, even when the cells were washed free of the conjugate on day 5 and were restimulated with anti-CD3 and IL-2 to induce continued cell proliferation.

In summary, these results demonstrated that wild-type PAP inhibits HIV-1 replication, and that PAP targeted to CD4+ T cells by conjugation with monoclonal antibody to CD4 is uniquely active at picomolar concentrations. Anti-CD4-PAP is about 5000 times more potent than non-conjugated PAP. Furthermore, anti-CD4-PAP is very effective at inhibiting HIV-1 production for at least several weeks in patients' activated CD4+ T cells and has an in vitro therapeutic index of approximately 1,000.

10. In Vitro Anti-Viral Activity of Anti-CD4-PAP Against Clinical HIV-1 Isolates A total of 22 clinical HIV-1 isolates were studied, including 8 isolates from four seropositive asymptomatic individuals, 6 isolates from three patients with the AIDS-related complex, and 8 isolates from four patients with AIDS (two pairs of zidovudine-resistant and zidovudine-susceptible reference isolates were also included in this group). Erice et al., *Antimicrob. Ag. Chemother.,* 37, 835 (1993). Fifteen isolates were from untreated individuals, and seven isolates were obtained after 24 to 104 weeks of treatment with zidovudine, alone or alternating with zalcitabine. The mean zidovudine $IC_{50}$ for strains from zidovudine-untreated individuals was 126 nM (range, 1 to 607 nM), and the mean zidovudine $IC_{50}$ for strains from zidovudine-treated patients was 2,498 nM (range, 14 to 6,497 nM). The mean αCCD4-PAP $IC_{50}$ for the 15 HIV-1 strains from zidovudine-untreated individuals was $48\times10^{-3}$ nM (range, $0.02\times10^{-3}$ to $212\times10^{-3}$ nM), and the mean αCD4PAP of the 7 HIV-1 strains from zidovudine-treated patients was $16\times10^{-3}$ nM (range, $2\times10^{-3}$ to $28\times10^{-3}$ nM). All eight HIV-1 isolates from seropositive asymptomatic individuals were susceptible to zidovudine, with a mean $IC_{50}$ of 150 nM (range, 1 to 607 nM) for isolates from zidovudine-untreated patients and an $IC_{50}$ of 14 nM for one isolate obtained after 48 weeks of zidovudine therapy. The mean αCD4-PAP $IC_{50}$s in this group were $11\times10^{-3}$ nM (range, $2.5\times10^{-3}$ to $25\times10^{-3}$ nM) for isolates from zidovudine-untreated individuals and $9\times10^{-3}$ nM for the isolate obtained after 48 weeks of zidovudine therapy. In the group of HIV-1 strains from patients with the AIDS-related complex, four isolates were zidovudine susceptible (mean zidovudine $IC_{50}$, 106 nM; range, 24 to 150 nM), whereas two isolates obtained after 52 weeks of therapy were resistant to zidovudine ($IC_{50}$s 1,710 to 2,137 nM). The mean αCD4-PAP $IC_{50}$s in this group were $24\times10^{-3}$ nM (range, $0.02\times10^{-3}$ to $46\times10^{-3}$ nM) for isolates from untreated individuals and $11\times10^{-3}$ nM for isolates obtained after 52 weeks of therapy. Five HIV-1 strains from patients with AIDS were zidovudine susceptible, with a mean zidovudine $IC_{50}$ of 105 nM (range, 44 to 166 nM). Three isolates from this group obtained after 24 to 104 weeks of treatment with zidovudine, alone or alternating with zalcitabine, were highly resistant to zidovudine. The mean αCD4-PAP values in this group were $137\times10^{-3}$ nM (range, $39\times10^{-3}$ to $212\times10^{-3}$ nM) for isolates from untreated individuals and $19\times10^{-3}$ nM (range, $2\times10^{-3}$ to $42\times10^{-3}$ nM) for isolates from treated patients. Overall, 17 isolates were susceptible to zidovudine (mean $IC_{50}$, 117 nM) and 5 were resistant to zidovudine (mean $IC_{50}$, 3,724 mM; for one isolate, the $IC_{50}$ could not be calculated but was >4,000 n). The mean αCD4-PAP values were $43\times10^{-3}$ nM for the 17 isolates susceptible to zidovudine and $19\times10^{-3}$ nM for the 5 isolates that were resistant to zidovudine. All of the HIV-1 isolates studied had $IC_{50}$s greater than 0.5 nM for unconjugated PAP, the αCD19-PAP immunoconjugate, and monoclonal antibody αCD4. In 18 αCD4-PAP experiments, cell viability ranged from 97.5% (for cells not exposed to the immunoconjugate) to 87.2% (for cells exposed to 5 nM αCD4-PAP). Cell viabilities in 22 zidovudine susceptible assays ranged from 90.9% (cells not exposed to zidovudine) to 90.75% (cells exposed to 10,000 mM zidovudine). At concentrations as high as 5,000 nM, αCD4-PAP did not inhibit colony formation by normal bone marrow progenitor cells (BFU-E, CFU-GM, and CFU-GEMM) or myeloid cell lines (KG-1 and HL-60) and did not decrease the viabilities of T-cell (Jurkat) or B-cell (FL-1 12 and Raji) precursor lines. Mild inhibition of Jurkat cells, CFU-GEMM, and CFU-GM was seen at a 15,000 nM concentration of αCD4-PAP (29, 11, and 12%, respectively).

There was a marked heterogeneity in the susceptibilities of HIV-1 isolates to zidovudine (range of $IC_{50}$s, 1 to 6,497 nM), as well as to αCD4-PAP (range of $IC_{50}$s $0.02\times10^{-3}$ to $212\times10^{-3}$ nM). Although αCD4-PAP exhibited a wide range of $IC_{50}$s against the clinical HIV-1 isolates studied, our results indicate that higher concentrations of the immunoconjugate were necessary to inhibit HIV-1 strains from untreated individuals who were at more advanced stages of HIV-1 related disease. We were able to evaluate seven paired HIV-I isolates obtained before and 24 to 104 weeks after initiation of antiretroviral therapy with zidovudine or alternating zidovudine and zalcitabine. In all cases, HIV-1 strains became less susceptible to zidovudine, with isolates obtained at later time points showing 1.6- to >91-fold increases in zidovudine $IC_{50}$s and five isolates becoming highly resistant to zidovudine. Intriguingly, six of seven HIV-1 strains obtained from treated individuals were more susceptible to αCD4-PAP, with 1.4- to 89.0-fold lower αCD4-PAP $IC_{50}$s than HIV-1 isolates from the same patients obtained prior to antiretroviral therapy. Whereas αCD4-PAP effectively inhibited the replication of HIV-1, controls (including unconjugated PAP, the αCD19-PAP immunoconjugate, and monoclonal antibody αCD4) did not, indicating that the anti-HIV-1 activity of αCD4-PAP requires both the CD4 antigen-specific monoclonal antibody moiety and the antiviral PAP moiety.

11. In vivo anti-HIV-1 activity of anti-CD4-PAP in the Hu-PBL-SCID mouse model of human AIDS Mutant C.B.17 mice are used as model systems to examine the in vivo homing, engraftment, and growth patterns of normal and malignant human hematopoietic cells. Uckun et al., *Blood,* 79, 2201 (1992). Severe combined immunodeficient (SCID) mice, reconstituted with human peripheral blood leukocytes (hu-PBL-SCID mice), have inducible human immune function and have been shown to be useful as a surrogate model for AIDS. Mosier et al., *Science* 251, 791 (1991). Hu-PBL-SCID mice could be infected with multiple strains of HIV-1 and infected mice contained virus that was recoverable by culture from the peritoneal cavity, spleen, peripheral blood, and lymph nodes for up to 16 weeks after infection. Mosier et al., cited supra. As detailed in the Preliminary Studies, we have used this model to compare the anti-viral activities of ZDV and anti-CD4-PAP against clinical HIV-1 isolates in vivo. Hu-PBL-SCID mice were generated by reconstituting SCID mice by intraperitoneal injection of $10\times10^6$ peripheral blood mononuclear cells from a single EBV-seronegative volunteer donor. Two weeks after inoculation of cells, mice were challenged by intraperitoneal injection of $1.47.–7\times10^4$ median tissue culture infectious doses ($TCID_{50}$) of cell free virus. Three different clinical HIV-1 strains (AT-101, AT-328, AT-332) were used. These isolates were recovered from peripheral blood leukocytes of HIV-1 infected individuals participating in National Institutes of Health-sponsored AIDS clinical trials at the University of Minnesota, as previously described by Jackson et al. in *J. Clin. Microbiol.,* 28, 16 (1990). SCID mice were infected with HIV-1 isolates in a Biosafety Level 3 containment facility and all manipulations were performed in a biosafety cabinet. Non-toxic doses of anti-CD4-PAP (20% –50% of $LD_{10}$) were administered intraperitoneally by injecting half of the total dose as a bolus and delivering the remainder i.p. over 2 weeks using Alzet micro-osmotic pumps. ZDV was added to the water at 1 mg/mL final concentration (this results in an average consumption of 200 mg/kg/day of ZDV). Two weeks after infection with HIV-1, mice were electively killed and fresh peritoneal lavage cells as well as spleen cells were isolated, cocultured with phytohemagglutinin(PHA)-stimulated human peripheral blood mononuclear cells from an HIV-1 antibody negative donor, and culture supernatants were tested every 3–4 days for a maximum of 28 days for the presence of HIV-1 antigen with a commercially available enzyme immunoassay (Abbott Laboratories, North Chicago, Ill.) that detects primarily the core p24 antigen of HIV-1, as previously described by Goudsmit et al. in *J. Infectious Diseases,* 155, 558 (1987). In addition to this culture method, we also isolated the DNA from the peritoneal lavage cells as well as splenocytes for detection of HIV-1 DNA by PCR amplification of a 115 b.p. sequence in the gag region of the HIV-1 genome using two 29-base oligonucleotide primers, SK38 and SK39, that flank the region to be amplified. Ou C-Y et al., *Science,* 239, 295 (19??). DNA samples were also examined for the presence of human DNA by PCR amplification of a 110-bp fragment from the first exon of the human β-globin gene using two 20-base oligonucleotide primers, PCO3 and PCO4, that flank the region to be amplified, as previously described in detail by Chelstrom et al. *Blood,* 84, 20 (1994). Furthermore, in some experiments we also used multiparameter flow cytometry to detect gp120 on CD4+ human T-cells isolated from the peritoneal cavity of HIV-1-infected Hu-PBL-SCID mice. Of the 23 Hu-PBL-SCID mice infected with HIV-1, and treated with PBS (a) 11 were analyzed by both HIV-culture and HIV-PCR and 10 were positive in both assays while one was only positive by PCR, (b) 6 were analyzed by HIV-culture only and all 6 were positive, (c) 6 were analyzed by HIV-PCR only and all 6 were positive. By contrast, no false positive results by HIV-culture or HIV-PCR in any of the 17 control Hu-PBL-SCID mice that were not injected with HIV-1. Viral genomes were detected by PCR in all 4 Hu-PBL-SCID mice treated with anti-CD4-PAP at a total dose of 20 μg but no virus was recovered by culture from any of these mice. Notably, HIV-1 DNA was detected in only 3 of 18 Hu-PBL-SCID mice treated with anti-CD4-PAP at a total dose of 40 μg and none of the 11 mixed peritoneal lavage+splenocyte cultures from these mice were positive. Similarly, no culture or PCR evidence of HIV- 1 infection was found in any of the 5 Hu-PBL-SCID mice treated with 60 μg anti-CD4-PAP. Importantly, CD4+gp120-T-cells were detected by multiparameter flow cytometry in the peritoneal lavage of anti-CD4-PAP treated mice and the presence of human DNA in spleen as well as peritoneal cavity was confirmed by β-globin gene PCR. Thus, the absence of HIV-1 in anti-CD4-PAP treated Hu-PBL-SCID mice was not caused by absence of human CD4+ T-cells due to poor engraftment or anti-CD4-PAP cytotoxicity. In contrast to anti-CD4-PAP treated mice, only 3 of 10 Hu-PBL-SCID mice treated with ZDV were HIV-1 negative. Of the remaining 7 mice, 4 were culture-positive and PCR positive, and 3 cases were culture-negative but PCR-positive. Notably, of the 8 Hu-PBL-SCID mice treated with a combination of anti-CD4-PAP and ZDV, none were culture-positive , none (of 5 analyzed) were PCR-positive in the peritoneal cavity-derived cells, and only 3 (of 8 analyzed) were PCR-positive in the spleen. These results are clearly superior to those obtained with ZDV alone and indicate that anti-CD4-PAP and ZDV do not have antagonistic interactions.

12. Conclusions

Since wild-type PAP-containing immunotoxins have been found to be very effective against human cancer xenografts in SCID mice and against leukemia and lymphoma in human patients, the immunotoxins and fusion toxins prepared using recombinant (variant) PAP are also expected to be effective in these treatments. Additionally, since PAP and PAP immunoconjugates have also been shown in the above examples to be effective against AIDS, it is expected that the immunoconjugates prepared utilizing recombinant PAP will also be effective in these treatments. Furthermore, it is contemplated that the PAP mutants of the present invention will have exhibit an improved therapeutic index over immunoconjugates containing either wild-type PAP or variant PAP since it is expected that they will have less cytotoxicity while retaining the full antiviral activity of wild-type PAP.

EXAMPLE 9

Construction and Purification of Biotherapeutic Agents

1. Immunoconjugates a. Anti-CD4-PAP

Affinity purified B53/TXU-5 (IgGl, αCD4) MoAb will be conjugated to 2-iminothiolane-modified PAP from spring leaves of Phytolacca americana or PAP mutants using the heterobifunctional crosslinking agent N-succinimidyl 3-(2-pyridyldithio) propionate (SPDP), according to procedures previously described by Zarling et al. and Uckun et al. *Nature,* 347, 92 (1990); *Journal of Experimental Medicine,* 163, 347 (1986), respectively. αCD4-PAP immunoconjugate will then be purified from unconjugated αCD4-MoAb and free PAP by size exclusion HPLC and cation exchange chromatography, as previously described in detail. Uckun et al., cited supra. The purity, composition, immunoreactivity, and ribosome inhibitory activity of αCD4 PAP immunoconjugates will be determined, as previously reported and described in more detail herein below. Uckun et al., cited supra. Controls will include unconjugated PAP, B43 (αCD19)-PAP directed against B-cells, and unconjugated α-CD4 antibody. These control reagents were prepared using previously published procedures. Uckun et al., cited supra.

2. Fusion Proteins a. PAP-GMCSF

The biotherapeutic agent expression vector pET11d-PAP-GMCSF will be constructed in three major steps. An 392 bp NcoI—BamHI DNA fragment containing the coding sequence of mature hGMCSF will be cloned between the Nco I and Bam HI sites of plasmid pET11d downstream of the T7 promoter to produce pET11d-GMCSF. PCR will be employed for mutagenesis of the mutant PAP toxin gene to provide coding sequences for a translation initiation ATG codon, a seven residue linker segment for fusion with the GMCSF gene, and convenient flanking NcoI restriction enzyme sites for cloning. PCR mutagenesis primers included a 5' primer: (5'-GGCATGGGCGCTGATGATGTTGTTGATTC-3') (SEQ ID NO:3) introducing an NcoI restriction enzyme site and ATG codon, and a 3' primer (5'GCG-TATTCTCCGGGGCATAAAATCGGGTGGAGGTGGCT-CCATGGC-3') (SEQ ID NO: 4) incorporating sequences encoding a linker domain for steric spacing of the GMCSF gene and an NcoI restriction enzyme site. Expression plasmid pET11d-PAP-GMCSF will be constructed by the cloning of the intact PAP Nco I gene cassette into the Nco I site of pET11d-GMCSF. Cloning strategies and other genetic manipulations will be positioned to assure maintenance of the translational reading frame, and fidelity of PCR amplification and genetic constructions will be confirmed by DNA sequencing. Oligonucleotide primers will be synthesized with an Applied Biosystems 394 DNA synthesizer at the University of Minnesota Microchemnical Facility. A synthetic cDNA encoding human GMCSF using *E. coli* codon preferences was obtained from R & D Systems (Minneapolis, Minn.).

Plasmid DNAs will be prepared by either the alkaline lysis method with purification on cesium chloride/ethidium bromide gradients, or by use of the Wizard DNA purification resin (Promega, Madison, Wis.). DNA fragments amplified by PCR will be initially cloned into the pT7Blue vector as directed by the manufacturer (Novagen), with DNA sequencing conflmation by the dideoxy method of Sanger using CircumVent thermal cycling reagents (New England Biolabs, Beverly, Mass.). Restriction endonucleases, Taq DNA polymerase, and T4 DNA ligase will be procured from BRL-Life Technologies (Gaitherburg, Md.), Promega, New England Biolabs, or Perkin Elmer (Norwalk, Conn.), and used according to the specifications directed by the manufacturer. Standard techniques will be employed for other manipulations of DNA including agarose gel electrophoresis, isolation and purification of restriction endonuclease fragments, cloning, and plasmid transformation into bacteria. [Sambrook et al., Molecular Cloning: A Laboratory Manual, 2nd ed. Cold Spring Harbor Laboratory Press, Cold Spring Harbor, N.Y., 1989].

b. PAP-B43

Gene cassettes encoding a B43 scFv with either a $V_LV_H$ or a $V_HV_L$ orientation will be constructed, since one cannot predict a priori which orientation would recreate the native B43 binding site with the greatest affinity. In addition, each of the $V_LV_H$ or $V_HV_L$ B43 scFv gene cassettes will be constructed in two versions, with two alternative linkers to connect the $V_L$ and $V_H$ cDNAs. The use of these two alternate linkers will permit identification of the B43 scFv versions that recreate the greatest affinity recombinant B43 binding when the scFv is fused with PAP-v toxin or other molecules.

The anti-human CD19 monoclonal antibody B43 (murine IgG, kappa) has been previously described by Uckun et al., *Blood,* 71, 13 (1988). Random oligonucleotide priming of messenger RNA isolated from the B43 production hybridoma will be used to produce cDNA with reverse transcriptase. Specific B43 $V_H$ and $V_L$ cDNA is produced by PCR using primers based on the B43 $V_H$ and $V_L$ sequences and incorporating novel additional restriction endonuclease sequences at the 5' and 3' termini of the antibody gene sequences. The primer sequences include:

PVH5'-1: 5'-GCC-ATG-GTT-CAG-CTG-CAG-CAG-TCT-GGG-GCT-GAG-C-3' (SEQ ID NO: 5)

PVH3'-1: 5'-CCA-TGG-CTA-TGA-GGA-GAC-GGA-GAC-TGA-GGT-TCC-TTG-3' (SEQ ID NO: 6)

PVL5'-1: 5'-GCC-ATG-GAC-ATT-GTG-CTG-ACC-CAA-TCT-CCA-GCT-TCC-3'(SEQ ID NO: 7)

PVL3'-1: 5'-CCA-TGG-CTA-TTT-GAT-TTC-CAG-CTT-GGT-GCC-TCC-ACC-GAA-CG-3' (SEQ ID NO: 8)

The restriction endonuclease cleavage sites that will be incorporated into the individual B43 $V_H$ and $V_L$ cDNA fragments are underscored. B43 $V_H$ and $V_L$ cDNAs will be individually cloned into standard TA vectors (Invitrogen Corp., San Diego Calif.) for the determination of DNA sequence by thermal cycle sequencing technology employing dideoxy chain termination methodology.

Construction of the B43 $V_LV_H$ and $V_HV_L$ scFv gene cassettes will be accomplished by genetic fusion of the cDNA sequences for the respective $V_LV_H$ and $V_HV_L$ scFv gene segments with the introduction of novel linking sequences. For each B43 $V_LV_H$ or $V_HV_L$ scFv gene cassette, two different genetic fusion will be constructed, each employing one of two different linkers to connect the $V_L$ and $V_H$ cDNAs. The unique version "A" linker encodes "Gly-Gly-Gly-Gly-Ser-Gly-Gly-Gly-Gly-Thr-Gly-Gly-Gly-Gly-Ser" (SEQ ID NO: 9), and the unique version "B" linker encodes "Gly-Ser-Thr-Ser-Gly-Ser-Gly-Lys-Ser-Ser-Glu-Gly-Lys-Gly" (SEQ ID NO: 10).

PCR mutagenesis will be employed to produce unique $V_L$ and $V_H$ cDNAs that are thus individually modified to include the addition of unique sequences to encode linkers between the $V_L$ and $V_H$ cDNAs. Overlapping PCR will then be employed to then produce B43 $V_LV_H$ and $V_HV_L$ scFv cassettes.

The detail of the primers for overlapping PCR is as follows:

PVL5'-1LA: 5'-TCC-GGA-GGA-GGC-GGT-ACC-GGT-GGT-GGC-GGT-AGC-GAC-ATT-GTG-CTG-ACC-CAA-TC-3' (SEQ ID NO: 11)

VL5'-1LB: 5'-CT-GGT-TCC-GGA-AAA-TCT-TCT-GAA-GGT-AAA-GGT-GAC-ATT-GTG-CTG-ACC-CAA-TC-3' (SEQ ID NO: 12)

PVH3'-1LA: 5'-ACC-GGT-ACC-GCC-TCC-TCC-GGA-TCC-GCC-TCC-GCCTGA-GGA-GAC-GGA-GAC-TG-3' (SEQ ID NO: 13)

PVH3'-1LB: 5'-C-AGA-AGA-TTT-TCC-GGA-ACC-AGA-GGT-AGA-ACC-TGA-GGA-GAC-GGA-GAC-TG-3' (SEQ ID NO: 14)

The predicted encoded sequence of the "A" and "B" versions of the linkers in the B43 $V_LV_H$ and $V_HV_L$ scFv cassettes is as follows:

LINKER A (SEQ ID NO: 15):

GGC-GGA-GGC-GGA-TCC-GGA-GGA-GGC-GGT-ACC-GGT-GGT-GGC-GGT-AGC CCG-CCT-CCG-CCT-AGG-CCT-CCT-CCG-CCA-TGG-CCA-CCA-CCG-CCA-TCG GLY-GLY-GLY-GLY-SER-GLY-GLY-GLYGLY-THR-GLY-GLY-GLY-GLY-SER

LINKER B (SEQ D NO: 16):

GGT-TCT-ACC-TCT-GGTTCC-GGA-AAA-TCT-TCT-GAA-GGT-AAA-GGT CCA-AGA-TGG-AGA-CCA-AGG-CCT-TTT-AGA-AGA-CTT-CCA-TTT-CCA GLY-SER-THR-SER-GLY-SER-GLY-LYS-SER-SER-GLU-GLY-LYS-GLY

The B43 $V_LV_H$LA, $V_LV_H$LB, $V_HV_L$LA and $V_HV_L$LB scfv cassettes will each be individually cloned into standard TA vectors for the determination of DNA sequence by thermal cycle sequencing technology employing dideoxy chain termination methodology.

The biotherapeutic agent expression vectors pET11d-PAP-B43 $V_LV_H$LA, $V_LV_H$LB, $V_HV_L$LA and $V_HV_L$LB will be each constructed in three major steps. Briefly, an NcoI DNA fragment containing the coding sequence of each B43 scFv cassette is cloned into the Nco I site of plasmid pET11d downstream of the T7 promoter to produce pET11d-B43 $V_LV_H$LA, $V_LV_H$LB, $V_HV_L$LA or $V_HV_L$LB. PCR will be employed for mutagenesis of the mutant PAP toxin gene to provide coding sequences for a translation initiation ATG codon, a seven residue linker segment for fusion with the B43 gene, and convenient flanking NcoI restriction enzyme sites for cloning. PCR mutagenesis primers will include a 5' primer (5'-GGCATGGGCGCTGATGATGTTGTTGATTC-3') (SEQ ID NO: 17) introducing an NcoI restriction enzyme site and ATG codon, and a 3' primer (5'GCGTATTCTCCGGGGCATAAAATCGGGTGGAGG-TGGCTCCATGGC-3') (SEQ ID NO: 18) incorporating sequences encoding a linker domain for steric spacing of the scFv cassette and an NcoI restriction enzyme site. Each PAP-B43 $V_LV_H$LA, $V_LV_H$LB, $V_HV_L$LA and $V_HV_L$LB expression plasmid will be constructed by the cloning of the intact DT Nco I gene cassette into the Nco I site of the respective pET11d-B43. Cloning strategies and other genetic manipulations will be positioned to assure maintenance of the translational reading frame, and fidelity of PCR amplification and genetic constructions will be confirmed by DNA sequencing. Oligonucleotide primers will be synthesized with an Applied Biosystems 394 DNA synthesizer at the University of Minnesota Microchemical Facility.

EXAMPLE 10

Expression of Fusion Proteins in *E. coli* and Subsequent Purification

1. PAP-GMCSF

*E. coli* HMS174(de3)plysS transformed with pET11dPAP-GMCSF will be grown at 37° C. in LB medium with carbenicillin (50 μg/ml) to an absorbance (Å600) of 0.4–0.6. Expression of the fusion gene will be induced by the addition of isopropyl-B-D-thiogalactopyranoside (IPTG) to a final concentration of 0.5 mM. The bacterial cells will be collected by centrifugation after one hour of induction, and resuspended in 50 mM potassium phosphate, 10 mM EDTA, 750 mM NaCl, 0. 1 % Tween 20, pH 8.0. Lysis of the cells will be achieved by freezing in a dry ice/ethanol bath followed by thawing and sonication. The soluble extract will be filtered through a 0.2 μm filter (Millipore, Bedford, Mass.) and applied to a 4 ml anti-PAP toxin immunoaffinity column.

The immunoaffinity column will be prepared with Affinica Antibody orientation Kit (Schleicher and Schuell, Keene, N.H.) using rabbit anti-PAP. Bound proteins will subsequently be eluted from the immunoaffinity column with 4M guanidine hydrochloride, 100 mM potassium phosphate, 0.1% Tween 20, pH 7.2. Eluate fractions containing the fusion toxin will be dialyzed in 20 mM Tris, 150 mM NaCl, pH 7.5 with 5 buffer changes over 18 hrs using 12 kD exclusion dialysis tubing. The dialyzed fusion toxin will be applied onto a Mono Q HR 5/5 chromatography column (Pharmacia, Piscataway, N.J.) and eluted at a flow rate of 1 ml/min over 30 min with a linear gradient of NaCl (150–500 mM in 20 mM Tris, pH 7.5). The purified fusion toxin will be concentrated 10–20 fold in a 30 kD exclusion filter (Amicon) followed by exhaustive dialysis in 2L PBS with 5 buffer changes over 18 hrs. Protein concentration will be determined by Bio-Rad Protein Assay. Over 100 μg of purified PAP-GMCSF protein is expected to be obtained from 1 liter pilot cultures.

2. PAP-B43

*E. coli* HMS 174(de3)plysS transformed with pET11dPAP-B43 will be grown at 37° C. in medium with carbenicillin (50 μg/ml) to an absorbance (Å600) of 0.4–0.6. Expression of the fusion gene will be induced by the addition of isopropyl-B-D-thiogalactopyranoside (IPTG) to a final concentration of 0.5 mM. The bacterial cells will be collected by centrifugation after one hour of induction, and resuspended in 50 mM potassium phosphate, 10 mM EDTA, 750 mM NaCl, 0.1% Tween 20, pH 8.0. Lysis of the cells will be achieved by freezing in a dry ice/ethanol bath followed by thawing and sonication.

The soluble extract will be filtered through a 0.2 μm filter (Millipore, Bedford, Mass.) and applied to a 4 ml anti-diphtheria toxin immunoaffmity column. The immunoaffmity column will be prepared with Affinica Antibody orientation Kit (Schleicher and Schuell, Keene, N.H.) using rabbit anti-PAP. Bound proteins will be subsequently eluted from the immunoaffinity column with 4M guanidine hydrochloride, 100 mM potassium phosphate, 0.1% Tween 20, pH 7.2. Eluate fractions containing the fusion toxin will be dialyzed in 20 mM Tris, 150 mM NaCl, pH 7.5 with 5 buffer changes over 18 hrs using 12 kD exclusion dialysis tubing. The dialyzed fusion toxin will be applied onto a Mono Q HR 5/5 chromatography column (Pharmacia, Piscataway, N.J.) and eluted at a flow rate of 1 ml/min over 30 min with a linear gradient of NaCl (150–500 mM in 20 mM Tris, pH 7.5). The purified fusion toxin will be concentrated 10–20 fold in a 30 kD exclusion filter (Amicon) followed by exhaustive dialysis in 2L PBS with 5 buffer changes over 18 hrs. Protein concentration will be determined by Bio-Rad Protein Assay.

EXAMPLE 11

Biochemical Characterization of Biotherapeutic Agents

1. Immunoconjugates a. Anti-CD4-PAP

SDS-PAGE (5% separating gel) will be used routinely to monitor the purity and composition of the immunoconjugate preparations, as previously reported by Uckun et al. *Journal of Experimental Medicine,* 163, 347 (1986). Gels will be stained with Coomassie Blue G-250, destained in 10% acetic acid/30% methanol, dried, and subsequently scanned using a Beckman DU62 spectrophotometer and Gel Scan Soft-Pac Module (Beckman Instruments). In addition, a silver stain kit obtained from Bio-Rad Laboratories will be used to visualize the protein bands after SDS-PAGE with greater sensitivity of detection. Uckun et al., cited supra. The presence of TXU-5/anti-CD4 monoclonal antibody and PAP-v moieties in the anti-CD4-PAP immunoconjugates will be confirmed using Western blot analysis and a detection kit obtained from Bio-Rad Laboratories, as previously described. Uckun et al., cited supra. The anti-PAP primary antibody will be generated in rabbits which have been hyperimmunized with highly purified PAP. Immunoblotting will also be done using alkaline phosphatase-conjugated goat anti-mouse IgG (Sigma Chemical Co., St. Louis, Mo.) to detect unconjugated anti-CD4 monoclonal antibody remaining in the purified immunoconjugate preparations. Uckun et al., cited supra. Protein concentrations will be determined using the Bicinchoninic Assay System obtained from Sigma Chemical Co. (St. Louis, Mo.). The ribosome-inhibiting activity of the mutant PAP moiety in the anti-CD4-PAP immunoconjugates will be analyzed in an mRNA-dependent cell-free translation system obtained in kit form from Promega Biotech inc. (Madison, Wis.) as reported previously by Uckun et al., cited supra. The inmmunoreactivity of the purified anti-CD4-PAP-v immunoconjugates with healthy normal as well as HIV-1 infected T-cells will be determined by two-color quantitative immunofluorescence and multiparameter flow cytometry, by the method previously described by Uckun et al. *Proc. Natl. Acad. Sci. U.S.A.,* 85, 8603 (1988).

2. Fusion Proteins

For biochemical characterization of the fusion proteins of the present invention, sodium dodecyl sulfate-polyacrylamide gel electrophoresis (SDS-PAGE) and Western blot analyses using rabbit anti-PAP antibodies will be performed by standard methods using 10–15% gels in a Mini-Protean II gel apparatus (Bio-Rad). PAP toxin and human cytokine or antibody standards will be obtained from Connaught Laboratories and R & D Systems (Minneapolis, Minn.), respectively. Primary antibodies will be used at a dilution of 1:5000. Secondary antibodies, covalently linked to horseradish peroxidase, will be used at a 1:10,000 dilution.

EXAMPLE 12

In Vitro Assays of Anti-HIV-1 Activity Against the LAV-$1^{BRU}$ Isolate of HIV-1

Effects of PAP, PAP mutants and immunoconjugates containing PAP or PAP mutants on HIV-1 p24 gag antigen production in CD4+ T-cells infected with LAV-$1^{BRU}$ isolate of HIV-1 (MOI=0.5; infection period=90 min) will be examined using a commercially available ELISA p24 antigen detection kit (Abbott Laboratories, North Chicago, Ill.). In addition, radioimmunoprecipitations will be performed using polyclonal anti-HIV human sera (Trimar) as previously described by Zarling et al. in order to demonstrate inhibition of HIV-1 protein expression in CD4+ T-cells treated with anti-CD4-PAP immunoconjugates. Zarling et al., *Nature,* 347, 92 (1990). We will also use a highly sensitive and quantitative reverse transcriptase-initiated PCR to measure the effects of PAP immunoconjugates on HIV-1 mRNA expression in CD4+ T-cells. Saksela et al., *Proc. Natl. Acad. Sci. U.S.A.,* 91, 1104 (1994). To control for the amount and integrity of the RNAs prepared from different PBMC samples, as well as the uniform efficiency of their reverse transcription, a β-actin mRNA-specific fragment will also be amplified from every cDNA preparation.

EXAMPLE 13

Preparation of Viral Stocks of Clinical HIV-1 Isolates

HIV-1 isolates will be recovered from peripheral blood specimens of HIV-1 infected patients participating in NIH-sponsored AIDS clinical trials at the University of Minnesota AIDS Clinical Trials Unit (ACTU), using a culture technique previously detailed by Erice et al. in *J. Clin. Microbiol.,* 30 444 (1992). In brief, $10\times10^6$ Ficoll-Hypaque separated mononuclear cells from seropositive patients will be co-cultured with $5\times10^6$ PHA-stimulated peripheral blood mononuclear cells from an HIV-1 seronegative healthy volunteer donor for 42 days at 37° C./5% $CO_2$ in 50 mL tissue culture flasks containing 15 mL RPMI 1640 supplemented with 20% fetal calf serum, 5% interleukin 2 (Cellular Products, Buffalo, N.Y.), 160 U/mL penicillin, and 160 μg/mL streptomycin. Co-culture supernatants will be assayed every 3–4 days for the presence of HIV-1 p24 gag antigen using a commercially available ELISA p24 antigen detection kit (Abbott Laboratories, North Chicago, Ill.), as previously reported by Goudsmit et al. *J. Infectious Diseases,* 155, 558 (1987). p24 antigen positive cultures will be expanded according to a standard protocol and aliquots of cell-free stock viruses will be prepared from supernatants of expanded cultures when the reverse transcriptase (RT) activity in the supernatant exceeds 20,000 cpm/50 μL. Schwartz et al., *AIDS Res. Hum. Retroviruses,* 4, 441 (1988). Some isolates will be recovered from frozen supernatants of p24 antigen positive cultures or from frozen cells of HIV-1 culture-positive patients. In these cases, normal donor peripheral blood mononuclear cells ($2–5\times10^6$ cells/mL) will be exposed for 2 h at 37° C./5% $CO_2$ to 1 mL of the p24 positive culture supernatant or $1\times10^6$ thawed peripheral blood mononuclear cells from HIV-1 culture positive patients and cultured in 50 mL tissue culture flasks. Subsequently, positive cultures will be expanded as described above.

EXAMPLE 14

Reverse Transcriptase (RT) Inhibition Assay

The in vitro susceptibility of clinical HIV-1 isolates to the PAP, PAP mutants, and anti-CD4 PAP immunoconjugates will be measured and compared using an RT inhibition assay, as described by Schwartz et al., cited supra. In brief, $5\times10^6$ PHA-stimulated seronegative donor peripheral blood mononuclear cells will be infected with HIV-1 by incubation in 1 mL of a stock virus preparation for 3 h at 37° C./5% $CO_2$. After infection, cells will be transferred to 96-well tissue culture plates (40 μL/well in triplicate wells) containing different concentrations of PAP or αCD4 PAP diluted in RPMI 1640 supplemented with 20% fetal calf serum, 5% interleukin 2 (Cellular Products), 160 U/mL penicillin, and 160 μg/mL streptomycin. αCD4 PAP treatment will continue for 5 days to mimic the FDA-approved clinical protocol of the ongoing phase II PAP immunoconjugate trials for treatment of B-lineage lymphoid malignancies (BB-IND #3864). At the end of the incubation period, culture supernatants will be removed and assayed for RT activity using the method of Schwartz and colleagues. Schwartz et al., cited supra. $IC_{50}$ values (concentration of drug needed to reduce RT activity by 50%) will be calculated from the RT activities of untreated versus treated samples using the SAS Regression Analysis Program (SAS Institute, Cary, N.C.). ZDV resistance will be defined as an ZDV-$IC_{50}$ value of greater than 1 μM. Standard statistical methods will be used including Student's t-tests to compare the αCD4 PAP sensitivity of ZDV-resistant and ZDV-sensitive HIV-1 isolates. All computations will be performed using an updated statistics program for the Macintosh (Statworks Statistics Program, Cricket Software, Philadelphia, Pa.).

EXAMPLE 15

Cytotoxicity Assays

Ficoll-Hypaque separated uninfected peripheral blood mononuclear cells ($5\times10^5$ cells/mL in RPMI 1640 supplemented with 5% fetal calf serum) from healthy volunteer donors will be incubated with different concentrations of PAP/PAP mutants or αCD4-PAP immunoconjugate for 5 days at 37° C. The viability of cells will be examined daily using a standard trypan-blue dye exclusion assay. In addition, viability of untreated, as well as αCD4-PAP treated cells, will be determined in triplicate by the same technique on the last day of each experiment examining the antiviral activity of αCD4- PAP against clinical HIV-1 isolates. Normal peripheral blood samples will be procured from healthy volunteer donors after obtaining informed consent according to the guidelines of the University of mesota Committee on the Use of Human Subjects in Research. Different PAP mutants and immunoconjugates will be examined for their ability to induce apoptotic death of human umbilical vein endothelial cells, using an apoptosis assay system which has been previously described by Uckun et al.

in great detail. *Proc. Natl. Acad. Sci. USA,* 89,9005 (1992) (Sponsored by ED. Thomas). In addition, a simple in vitro model of capillary leak will be utilized as described by Soler-Rodriguez et al. Soler-Rodriguez et al., *Experimental Cell Research* 206, 227 (1993).

EXAMPLE 16

SCID Mouse Model of Human AIDS

Hu-PBL-SCID mice will be generated by reconstituting SCID mice by intraperitoneal injection of $10\times10^6$ peripheral blood mononuclear cells from a single EBV-seronegative volunteer donor. Two weeks after inoculation of cells, mice will be challenged by intraperitoneal injection of $1.4–7.7\times10^4$ median tissue culture infectious doses ($TCID_{50}$) of cell free virus. Three different clinical HIV-1 strains (AT-101, AT-328, AT-332) will be used. These isolates were recovered from peripheral blood leukocytes of HIV-1 infected individuals participating in National Institutes of Health-sponsored ADS clinical trials at the University of Minnesota, as previously described by Erice et al. *J. Clin. Microbiol.,* 30,444 (1992). SCID mice will be infected with HIV-1 isolates in a Biosafety Level 3 containment facility and all manipulations will be performed in a biosafety cabinet.

Escalating doses of PAP/PAP mutants or anti-CD4-PAP will be administered intraperitoneally by injecting half of the total dose as a bolus and delivering the remainder over 2 weeks using Alzet micro-osmotic pumps. Two weeks after infection with HIV-1, mice will be electively killed and fresh peritoneal lavage cells as well as spleen cells will be isolated, cocultured with phytohemagglutinin (PHA)-stimulated human peripheral blood mononuclear cells from an HIV-1 antibody negative donor, and culture supernatants tested every 3–4 days for a maximum of 28 days for the presence of HIV-1 antigen using a commercially available enzyme immunoassay (Abbott Laboratories, North Chicago, Ill.) that detects primarily the core p24 antigen of HIV-1, as previously described by Goudsmit et al., *J. Infectious Diseases.* 155, 558 (1987). In addition to this culture method, the DNA from the peritoneal lavage cells will also be isolated, as well as splenocytes for detection of HIV-1 DNA, by PCR amplification of a 115 b.p. sequence in the gag region of the HIV-1 genome using two 29-base oligonucleotide primers, SK38 and SK39, that flank the region to be amplified. Ou C-Y et al., *Science,* 239, 295 (19??). DNA samples will also be examined for the presence of human DNA by PCR amplification of a 11 0-bp fragment from the first exon of the human B-globin gene using two 20-base oligonucleotide primers, PCO3 and PCO4, that flank the region to be amplified, as previously described in detail by Uckun et al. *Leukemia* 7, 341 (1993); *Journal of Experimental Medicine,* 163, 347 (1986). Oligonucleotide primers (SK38: 5'ATA ATC CAC CTA TCC CAG TAG GAG AAA T3' and SK39: 5'TTT GGT CCT TGT CTT ATG TCC AGA ATG C3') will be synthesized by the University of Minnesota Microchemical Facility using an Applied Biosystems Synthesizer (Foster City, Calif.). HIV DNA will be amplified using 1.0 μg genomnic DNA with 2.5 U of Taq DNA Polymerase (Perkin-Elmer Cetus, Norwalk, Conn.) in 1×PCR buffer (50 mM KCl, 10 mM Tris-Cl pH 8.3,2.5 MM $MgCl_2$ and 0.01% wt/vol gelatin) containing 0.5 μM of each primer and 200 μM dNTP's (Pharmacia, Piscataway, N.J.) in a total volume of 100 μL. Before amplification, samples will be overlaid with 100 μl of mineral oil (Sigma, St. Louis, Mo.). Thirty cycles will be performed by incubating samples at 95° C. for 1 minute and 60° C. for 1 minute.

Oligomer hybridization will be used to detect PCR amplified-HIV DNA. Briefly, 30 μL of amplified DNA will be added to 10 μL of probe mix consisting of 0,2 pmol 32p-labeled SK19 (5'ATC CTG GGA TTA AAT AAA ATA GTA AGA ATG TAT AGC CCT AC 3'), 24 mm NaCl and 4 mM EDTA pH 8.0. Samples will be denatured in a 95° C. bath for 5 minutes followed by a 55° C. 15 minute incubation to anneal probe and target sequences. Ten microliters of bromophenol blue/xylene cyanol dye mix will be added to each tube and 25 μl of each sample will be analyzed on a 10% polyacrylamide gel in 1×TBE buffer (0.089M Tris-borate and 0.002M EDTA). Following electrophoresis, the gel will be dried and exposed to Kodak XAR-5 film for 2 hrs with an intensifying screen. Controls will include (a) the PCR reaction buffer without the genomic DNA, (b) PCR reaction product of DNA from HIV-1 injected but unreconstituted SCID mice as well as from uninfected Hu-PBL-SCID mice as negative background controls, and (c) HIV-1 control plasmid DNA (Perkin-Elmer Cetus, Norwalk, Conn.) as well as DNA from infected but untreated Hu-PBL SCID mice as positive DNA controls.

EXAMPLE 17

Pharmacologic Studies in Mice and Rabbits

All animal studies will be performed following the U.S. Government Principles for the Utilization and Care of Vertebrate Animals Used in Testing, Research, and Training and according to the guidelines of the University of Minnesota Animal Care Committee. Female BALBIc mice (6–8 weeks old, 15–20 grams) will be obtained from NIH or the SCID Mouse Breeding Facility of the Biotherapy Program and maintained in the ALAAC accredited facilities of the University of Minnesota Research Animal Resources. Mice will be lightly anesthetized with ether and injected i.v. with 50 μg of the anti-CD4-PAP immunoconjugates in 0.5 mL PBS. Mice will be serially bled by retroorbital puncture following administration of the immunoconjugates. New Zealand white female rabbits (3 kg) (River Valley Farms, Marine-on-St. Croix, Minn.) will be injected i.v. with 1 mg anti-CD4-PAP immunoconjugates in 0.5 mL PBS. Rabbits will be serially bled (500 μL/time point) from their external jugular veins following administration of the immunoconjugate. Highly sensitive solid phase ELISA assays will be used to determine plasma levels of intact anti-CD4-PAP imnnunoconjugates and total antibody (=intact immunotoxin plus free antibody) in these blood samples, as previously described by Uckun et al. *Journal of Experimental Medicine,* 163, 347 (1986). Free antibody data will be obtained by subtracting intact immunotoxin levels from total antibody levels.

A two compartment first-order pharmacokinetic model will be fit to the anti-CD4-PAP plasma concentration versus time data for SCIDI mice. For the rabbit data, two separate but linked two-compartment models, one for free antibody data and one for intact immunoconjugate data, will be simultaneously fit to the antibody and immunotoxin concentration-time data within the same animal. Maximum likelihood estimation, as implemented in ADAPT II Software, will be used to estimate the central volume of distribution (Vc), elimination rate constants ($K_{10}$ or $K_{30}$), and distribution rate constants ($K_{12}$, $K_{21}$ or $K_{34}$, $K_{43}$) for immunoconjugate and free antibody, respectively. D'Argenio et al., *Comput. Prog. Biomed.,* 9, 115 (1979). Systemic clearance of immunotoxin will be calculated as Vc x ($K_{10}+K_{13}$).

All patents and publications are incorporated by reference herein, as though individually incorporated by reference. Specifically, the U.S. Patent Application entitled "Pokeweed Antiviral Protein Mutants", by inventor Nilgun E. Turner, filed Jul. 11, 1995, now U.S. Pat. No. 5,756,322, issued May 26, 1998 and the U.S. Patent Application entitled "DNAs Encoding Pokeweed Antiviral Mutants", by inventor Nilgun E. Turner, also filed Jul. 11, 1995, now U.S. Pat. No. 5,880,329, issued Mar. 9, 1999, are incorporated herein by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A fusion protein comprising: mutant Pokeweed Antiviral Protein (PAP) having an amino acid substitution at residue 75, 97, or 176; and a targeting moiety that binds a cell surface receptor.

2. The fusion protein of claim 1, wherein said mutant PAP comprises amino acids 263 to 291 of native PAP.

3. The fusion protein of claim 1, wherein said mutant PAP comprises N-terminal signal peptide amino acids 1 to 22 of native PAP.

4. The fusion protein of claim 1, wherein said mutant PAP comprises Arg-20 and His 49.

5. The fusion protein of claim 1, wherein said mutant PAP comprises one or more substitution, deletion, or frameshift modification at amino acid Gly-75, Glu-176, Trp-208, Glu-184, Trp-237, Glu-97, or Leu-202.

6. The fusion protein of claim 1, wherein the targeting moiety is a monoclon antibody or portion thereof that specifically binds CD2, CD3, CD4. CD5, CD7, CD13, CD19, CD22, CD24, CD33, CD40, CD45, or CD72 antigen.

7. An immunoconjugate comprising:

mutant Pokeweed Antiviral Protein (PAP) having an amino acid substitution at residue 75, 97, or 176; and a targeting moiety that binds a cell surface receptor.

8. The immunoconjugate of claim 7, wherein said mutant PAP comprises amino acids 263 to 291 of native PAP.

9. The immunoconjugate of claim 7, wherein said mutant PAP comprises N-terminal signal peptide amino acids 1 to 22 of native PAP.

10. The imnmunoconjugate of claim 7, wherein said mutant PAP comprises Arg-20 and His-49.

11. The immunoconjugate of claim 7, wherein said mutant PAP comprises one or more substitution, deletion, or frameshift modification at amino acid Gly-75, Glu-176, Trp-208, Glu-184, frp-237, Glu-97, or Leu-202.

12. The immunoconjugate of claim 7, wherein the targeting moiety is a monoclonal antibody or portion thereof that specifically binds CD2, CD3, CD4, CD5, CD7, CD13, CD19, CD22, CD24, CD33, CD40, CD4S, or CD72 antigen.

* * * * *

UNITED STATES PATENT AND TRADEMARK OFFICE

CERTIFICATE OF CORRECTION

PATENT NO. : 6,146,628 
DATED : November 14, 2000
INVENTOR(S) : Uckun et al.

It is certified that error appears in the above-identified patent and that said Letters Patent is hereby corrected as shown below:

<u>Title page,</u>
Item [73], Assignees, delete "and Rutgers," and insert after the word "Minn.;" -- and Rutgers, --.

<u>Column 1,</u>
Line 6, "MCB-941919" should read -- MCB-9419919 --.

<u>Column 2,</u>
Lines 28-31, delete "an amino acid sequence according to SEQ ID NO:2, SEQ ID NO:3, SEQ ID NO:4, SEQ ID NO:5, SEQ ID NO:6, SEQ ID NO:7, SEQ ID NO:8" and insert therefore -- a point mutation that alters amino acid residue 75 from glycine (Gly75) to valine (Val75), alanine (Ala75), isolencine (Ile75) or alters amino acid residue 97 from glutamic acid (Glu97) to lysine (Lys97), or comprises the 22-amino acid N-terminal signal peptide (1-22) or the 29 amino acid C-terminal extension (263-291) --.

<u>Column 11,</u>
Line 33, Table I: "Gku" should read -- Glu --.
Line 44, Table I: "GCT" should read -- GGT --.
Line 56, Table I: "TTCCAA" should read -- TTC CAA --.

<u>Column 14,</u>
Line 26, "*Chemotherapv*" should read -- *Chemotherapy* --.

<u>Column 17,</u>
Line 3, "*Sci*, 24, 431" should read -- *Sci*, 284, 431 --.
Line 19, "p$^{5}$5" should read -- p55 --.

<u>Column 21,</u>
Line 41, "*Ouant*" should read -- *Quant* --.

<u>Column 22,</u>
Line 16, "lysinelarginine" should read -- lysine/arginine --.

<u>Column 23,</u>
Line 17, "lad" should read -- lacI --.

UNITED STATES PATENT AND TRADEMARK OFFICE

CERTIFICATE OF CORRECTION

PATENT NO. : 6,146,628
DATED : November 14, 2000
INVENTOR(S) : Uckun et al.

It is certified that error appears in the above-identified patent and that said Letters Patent is hereby corrected as shown below:

Column 25,
Lines 53-54, "Table 1" should read -- Table 2 --.
Line 66, "his3-1 1" should read -- his3-11 --.

Column 26,
Line 57, "Laenunlie" should read -- Laemmlie --.

Column 28,
Line 38, "1 24-1" should read -- 124-1 --.

Column 29,
Line 20, "ng/mi" should read -- ng/ml --.
Line 26, "HT123-2" should read -- HMNT-2 --.

Column 32,
Line 64, "CD19±" should read -- $CD19^+$ --.

Column 34,
Line 63, "103" should read -- $10^3$ --.

Column 35,
Line 45, "αCCD-4" should read -- αCD4 --.

Column 36,
Lines 22-23, "10,000 mM" should read -- 10,000 nM --.
Line 27, "(FL-1 12" should read -- (FL-112 --.

Column 37,
Line 12, "$1.47.-7x10^4$" should read -- $1.4-7.7x10^4$ --.

Column 39,
Lines 10-11, "(SEQ ID NO:3)" should read -- (SEQ ID NO:16) --
Line 14, "(SEQ ID NO:4)" should read -- (SEQ ID NO:17) --.
Line 25, "Microchemnical" should read -- Microchemical --.
Line 35, "conflmation" should read -- confirmation --.

UNITED STATES PATENT AND TRADEMARK OFFICE
CERTIFICATE OF CORRECTION

PATENT NO. : 6,146,628
DATED : November 14, 2000
INVENTOR(S) : Uckun et al.

It is certified that error appears in the above-identified patent and that said Letters Patent is hereby corrected as shown below:

Column 40,
Line 5, "(SEQ ID NO:5)" should read -- (SEQ ID NO:18) --
Line 7, "(SEQ ID NO:6)" should read -- (SEQ ID NO:19) --
Line 9, "(SEQ ID NO:7)" should read -- (SEQ ID NO:20) --
Line 11, "(SEQ ID NO:8)" should read -- (SEQ ID NO:21) --
Line 28, "(SEQ ID NO:9)" should read -- (SEQ ID NO:22) --
Line 30, "(SEQ ID NO:10)" should read -- (SEQ ID NO:23) --
Line 41, "(SEQ ID NO:11)" should read -- (SEQ ID NO:24) --
Line 44, "(SEQ ID NO:12)" should read -- (SEQ ID NO:25) --
Line 47, "(SEQ ID NO:13)" should read -- (SEQ ID NO:26) --
Line 50, "(SEQ ID NO:14)" should read -- (SEQ ID NO:27) --
Line 54, "(SEQ ID NO:15)" should read -- (SEQ ID NO:28) --
Line 59, "GLYGLY" should read -- GLY-GLY --
Line 60, "(SEQ D NO:16)" should read -- (SEQ ID NO:29) --
Line 61, "GGTTCC" should read -- GGT-TCC --
Line 67, "scfv" should read -- scFv --

Column 41,
Line 16, "(SEQ ID NO:17)" should read -- (SEQ ID NO:30) --
Line 19, "(SEQ ID NO:18)" should read -- (SEQ ID NO:31) --

Column 42,
Line 5, insert -- LB -- after the word "in"

Column 44,
Line 62, "mesota" should read -- Minnesota --

Column 45,
Line 18, "ADS" should read -- AIDS --
Line 46, "11 0-bp" should read -- 110-bp --
Line 59, "2.5 MM" should read -- 2.5 mM --

Column 46,
Line 3, "24 mm" should read -- 24 mM --
Line 26, "BALBIc" should read -- BALB/c --
Line 50, "SCIDI" should read -- SCID --
Line 66, "Turner" should read -- Tumer --

UNITED STATES PATENT AND TRADEMARK OFFICE

CERTIFICATE OF CORRECTION

PATENT NO. : 6,146,628
DATED : November 14, 2000
INVENTOR(S) : Uckun et al.

It is certified that error appears in the above-identified patent and that said Letters Patent is hereby corrected as shown below:

Column 47,
Line 3, "Turner" should read -- Tumer --

Column 59,
Line 31, "monoclon" should read -- monoclonal --

Column 60,
Line 27, "frp-237" should read -- Trp-237 --.

Signed and Sealed this

Third day of September, 2002

*Attest:*

JAMES E. ROGAN

*Attesting Officer*

*Director of the United States Patent and Trademark Office*